(12) United States Patent
Goetschi et al.

(10) Patent No.: US 8,389,717 B2
(45) Date of Patent: Mar. 5, 2013

(54) MODULATORS FOR AMYLOID BETA

(75) Inventors: Erwin Goetschi, Reinach (CH); Synese Jolidon, Blauen (CH); Thomas Luebbers, Loerrach (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/437,057

(22) Filed: Apr. 2, 2012

(65) Prior Publication Data

US 2012/0190682 A1 Jul. 26, 2012

Related U.S. Application Data

(63) Continuation of application No. 12/572,327, filed on Oct. 2, 2009, now abandoned.

(30) Foreign Application Priority Data

Oct. 9, 2008 (EP) .................................... 08166228

(51) Int. Cl.
C07D 401/14 (2006.01)
C07D 403/12 (2006.01)
C07D 403/14 (2006.01)
C07D 413/14 (2006.01)
A61K 31/4178 (2006.01)
A61K 31/53 (2006.01)
A61P 25/28 (2006.01)

(52) U.S. Cl. ........ 544/194; 544/197; 544/208; 544/218; 514/245

(58) Field of Classification Search .................. 544/194, 544/197, 208, 218; 514/245
See application file for complete search history.

(56) References Cited

U.S. PATENT DOCUMENTS

| | | | |
|---|---|---|---|
| 5,686,070 | A | 11/1997 | Doerschuk et al. |
| 6,399,773 | B1 | 6/2002 | Liu et al. |
| 2003/0176454 | A1 | 9/2003 | Yamada et al. |
| 2004/0034008 | A1 | 2/2004 | Stamford et al. |
| 2005/0176772 | A1 | 8/2005 | Calabrese et al. |
| 2006/0004013 | A1 | 1/2006 | Kimura et al. |
| 2007/0117798 | A1 | 5/2007 | Kimura et al. |
| 2007/0117839 | A1 | 5/2007 | Kimura et al. |
| 2007/0219181 | A1 | 9/2007 | Kimura et al. |
| 2008/0280948 | A1 | 11/2008 | Baumann et al. |
| 2009/0163485 | A1 | 6/2009 | Knust et al. |
| 2009/0181965 | A1 | 7/2009 | Baumann et al. |
| 2009/0215759 | A1 | 8/2009 | Baumann et al. |

FOREIGN PATENT DOCUMENTS

| | | |
|---|---|---|
| EP | 0233461 | 8/1987 |
| EP | 1201661 | 5/2002 |
| EP | 1479397 | 11/2004 |
| EP | 1950211 | 7/2008 |
| EP | 2019093 | 1/2009 |
| WO | 94/04487 | 3/1994 |
| WO | 97/21704 | 6/1997 |
| WO | 99/65884 | 12/1999 |
| WO | 00/25780 | 5/2000 |
| WO | 00/27842 | 5/2000 |
| WO | 00/78731 | 12/2000 |
| WO | 01/47897 | 7/2001 |
| WO | 01/87845 | 11/2001 |
| WO | 02/057240 | 7/2002 |
| WO | 03/002561 | 1/2003 |
| WO | 03/040141 A1 | 5/2003 |
| WO | 03/047512 | 6/2003 |
| WO | 03/053939 | 7/2003 |
| WO | 2004/046118 | 6/2004 |
| WO | 2004/069185 | 8/2004 |
| WO | 2004/087699 | 10/2004 |
| WO | 2004/110350 | 12/2004 |
| WO | 2005/003103 | 1/2005 |
| WO | 2005/013996 | 2/2005 |
| WO | 2005/040120 | 5/2005 |
| WO | 2005/044785 | 5/2005 |
| WO | 2005/063022 | 7/2005 |
| WO | 2005/115990 | 12/2005 |
| WO | 2006/040192 | 4/2006 |
| WO | 2006/058905 | 6/2006 |
| WO | 2006/111549 | 10/2006 |
| WO | 2006/112550 | 10/2006 |
| WO | 2006/112551 | 10/2006 |
| WO | 2007/051333 | 5/2007 |
| WO | 2007/053452 | 5/2007 |
| WO | 2007/054480 | 5/2007 |

(Continued)

OTHER PUBLICATIONS

Wilkins et al., Science of Synthesis 13:277-295 ( 2004).
Jantzen et al., Neuroscience 22:226-254 ( 2002).
Delecea et al., Proc. Natl. Acad. Sci. USA 95:322-327 ( 1998).
Sakamoto et al., Regul. Pept. 118:183-191 ( 2004).
Kumita et al., Nippon Noyaku Gakkaishi 26(1):60-66 ( 2001).
Takahashi et al., Biol. Chem. 278:18644-18670 ( 2003).
Dhar et al., Bioorganic & Medicinal Chemistry Letters (XP002522864), 12(12):3125-3128 ( 2002).
Suzuki et al., Brain Research 1044:116-121 ( 2005).
Yang et al., Org. Chem. vol. 67(21):7429-7431 ( 2002).

(Continued)

*Primary Examiner* — Venkataraman Balasubramanian
(74) *Attorney, Agent, or Firm* — George W. Johnston; Patricia S. Rocha-Tramaloni; Kimberly J. Prior

(57) ABSTRACT

The invention relates to compounds of formula

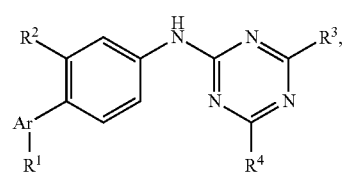

wherein $R^1$, $R^2$, R3, R4, and Ar are as defined in the specification and claims, or to pharmaceutically active acid addition salts of such compounds. Compounds of formula I are modulators for amyloid beta and may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

4 Claims, No Drawings

FOREIGN PATENT DOCUMENTS

| | | |
|---|---|---|
| WO | 2007/058304 | 5/2007 |
| WO | 2007/058305 | 5/2007 |
| WO | 2007/060810 | 5/2007 |
| WO | 2007/060821 | 5/2007 |
| WO | 2007/076161 | 5/2007 |
| WO | 2007/102580 | 9/2007 |
| WO | 2007/120333 | 10/2007 |
| WO | 2007/131953 | 11/2007 |
| WO | 2007/135969 | 11/2007 |
| WO | 2007/135970 | 11/2007 |
| WO | 2007/139149 | 12/2007 |
| WO | 2008/006103 | 1/2008 |
| WO | 2008/013213 | 1/2008 |
| WO | 2008/065626 | 6/2008 |
| WO | 2008/097538 | 8/2008 |
| WO | 2008/099210 | 8/2008 |
| WO | 2008/107096 | 9/2008 |
| WO | 2008/138753 | 11/2008 |
| WO | 2008/156580 | 12/2008 |
| WO | 2009/032277 | 2/2009 |
| WO | 2010/027500 | 2/2009 |
| WO | 2009/032861 | 3/2009 |
| WO | 2009/076337 | 6/2009 |
| WO | 2008/100412 | 8/2009 |
| WO | 2009/103652 | 8/2009 |
| WO | 2009/155551 | 12/2009 |
| WO | 2010/010184 | 1/2010 |
| WO | 2010/010188 | 1/2010 |
| WO | 2010/098487 | 9/2010 |

OTHER PUBLICATIONS

Perretto et al., Med. Chem. 48:5705-5720 ( 2005).
Clarke et al., Biol. Chem. 281:31279-31289 ( 2006).
(Office Action in copending U.S. Appl. No. 12/114,852 Jun. 28, 2010).
Kidwai et al., Chemical Papers:231-234 ( 2000).
Cai et al., Expert Opin. Ther. Patents 16(5):631-646 ( 2006).
Albaneze-Walker et al., Tetrahedron 61:6330-6336 ( 2005).
Piper et al., Eur. J. Neuroscience 12:726-730 ( 2000).
Winsky Sommerer et al., J. Neuroscience 24:11439-11448 ( 2004).
Menicagli et al., Synth. Commun. 24:2153-2158 ( 1994).
Ida et al., Biochem. Biophys. Res. Comm. 270:318-323 ( 2000).
Sakurai et al., Cell 92:573-585 ( 1998).
Patrick, Graham an Introduction to Medicinal Chemistry "10.3.9" Oxford, vol. 3rd edition:210-212.
Cooke et al., Tetrahedron 57:2787-2789 ( 2001).
Kuru et al., Neuroreport 11:1977-1980 ( 2000).
(EPO Communication in EP Appl. 09713519.8 Dec. 30, 2011).
Ringold et al., Am. Chem. Soc. 78:2477-2479 ( 1956).
Narlawar et al., Med. Chem. 49:7588-7591 ( 2006).
Schulte et al., Synlett:2331-2336 ( 2007).
Reinke, A. et al., Chem. Biol. Drug Des. 70:206-215 ( 2007).
(International Search Report PCT/EP 2008/055290 Oct. 8, 2008).
Siegel, Annu. Rev. Psychol. 55:125-148 ( 2004).
(Translation of Israeli Off Act in Corres Israeli App 206945 dated Feb. 29, 2012).
Beher et al., Biol. Chem. 279:43419-43426 ( 2004).
Nettekoven et al., Synthesis 11:1649-1652 ( 2003).
Iwanowicz et al., Bioorg. Med. Chem. Lett. 13:2059-2063 ( 2003).
Maiti et al., JOC Note 75:1791-1794 ( 2010).
Morihara et al., Neurochem. 83:1009-1012 ( 2002).
Grundmann et al., Am. Chem. Soc. 79:944-948 ( 1957).
Tilley et al., Helv. Chim. Acta 63:832-840 ( 1980).
Nilsson et al., J. Med. Chem. 46:3985-4001 ( 2003).
Pitts et al., Bioorganic & Medicinal Chemistry Letters 12(16):2137-2140 ( 2002).
Chang et al., Neurosci. Res. 56:356-362 ( 2006).
Nishino et al., Lancet 355:39-40 ( 2000).
Kukar et al., Nature Med. 11:545-550 ( 2005).
(International Search Report PCT/EP2009/064497 Apr. 8, 2010).
(International Search Report for PCT/EP2008/067273 May 15, 2009).
Paul et al., Jour. of Medicinal Chemistry (XP002522865), 36(19):2716-2725 ( 1999).
Caubere et al., Bull. Soc. Chim. Fr.:2112-2115 ( 1973).
Chemelli et al., Cell 98:437-451 ( 1999).
Malherbe et al., Mol. Pharmacol. 64:823-832 ( 2003).
McPhee et al., Med. Chem. Soc. 66:1132-1136 ( 1944).
Bingham et al., Current Opinion in Drug Discovery & Development 9(5):551-559 ( 2006).
Olson, R. et al., Current Topics in Medicinal Chemistry 8:17-33 ( 2008).
Lin et al., Cell 98:365-376 ( 1999).
(International Search Report for PCT/EP2009/062570 Dec. 4, 2009).
Dorwald F. A. Side Reactions in Organic Systhesis "1 & Preface" Wiley,:1-16 ( 2005).
Peyron et al., Nature Medicine 6:991-997 ( 2000).
Bourgin et al., J. Neurosci. 20(20):7760-7765 ( 2000).
(Office Action in copending U.S. Appl. No. 12/334,559 Sep. 30, 2009).
Lleo et al., Nature Med. 10:1065-1066 ( 2004).
Weggen et al., Nature 414:212-216 ( 2001).
(International Search Report for PCT/EP2009/051613 Apr. 22, 2004).
Hirt et al., Helv. 33:1365-1369 ( 1950).
Kubinyi 3D QSAR in Drug Design: Ligand Protein Interactions & Molecular SimilaritySpringer, vol. 2-3:243-244 ( 1998).
Mignot et al., Sleep 11:1012-1020 ( 1997).
Sakurai, Regulatory Peptides 126:3-10 ( 2005).
(Office Action in copending U.S. Appl. No. 12/334,559 May 20, 2010).
Peyron et al., Neurosci. 18:9996-10015 ( 1998).
Nambu et al., Brain Res. 18:243-260 ( 1999).
Bessard et al., Tetrahedron 55:405-412 ( 1999).
Smith et al., Neurosci. Lett. 341(3):256-258 ( 2003).
Schaeffer et al., Am. Chem. Soc. 73:2990-2992 ( 1951).
Stock et al., Bioorg. Med. Chem. Lett. 16:2219-2223 ( 2006).
Digby et al., J. Endocrinol. 191:129-136 ( 2006).
Wu et al., Tet. Lett. 49:2869-2871 ( 2008).
(Translation of Jap Off Act in Corres Jap App 200980139824 Dec. 5, 2012).

MODULATORS FOR AMYLOID BETA

PRIORITY TO RELATED APPLICATION(S)

This application is a continuation of U.S. application Ser. No. 12/572,327, filed Oct. 2, 2009, now pending; which claims the benefit of European Patent Application No. 08166228.0, filed Oct. 9, 2008. The entire contents of the above-identified applications are hereby incorporated by reference.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has loose substrate specificity and may cleave further membrane proteins unrelated to APP and Notch.

The γ-secretase activity is absolutely required for the production of Aβ peptides. This has been shown both by genetic means, i.e., ablation of the presenilin genes and by low-molecular-weight inhibitory compounds. Since according to the amyloid hypothesis for AD the production and deposition of Aβ is the ultimate cause for the disease, it is thought that selective and potent inhibitors of γ-secretase will be useful for the prevention and treatment of AD.

An alternative mode of treatment is the modulation of the γ-secretase activity which results in a selective reduction of the Aβ42 production. This will result in to an increase of shorter Aβ isoforms, such as Aβ38, Aβ37 or others, which have reduced capability for aggregation and plaque formation, and hence less neurotoxic. Compounds which show this effect on modulating γ-secretase activity include certain non-steroidal anti-inflammatory drugs (NSAIDs) and related analogues (Weggen et al. Nature, 414 (2001) 212-16).

Numerous documents describe the current knowledge on γ-secretase modulation, for example the following publications:

Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91

SUMMARY OF THE INVENTION

The invention provides compounds of formula I

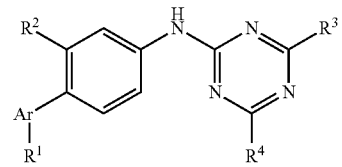

wherein
$R^1$ is hydrogen, lower alkyl or is lower alkyl substituted by hydroxy;
$R^2$ is hydrogen, lower alkoxy or lower alkyl;
$R^3$ and $R^4$ are each independently hydrogen, halogen, lower alkyl, C(O)O-lower alkyl, OR', NR"R''', lower alkyl substituted by halogen or hydroxy, or is phenyl or benzyl, each of which is optionally substituted by one or two halogen atoms;
R' is lower alkyl, or is phenyl, benzyl or pyridinyl, wherein phenyl, benzyl or pyridinyl are each optionally substituted by one or more halogen, lower alkyl or lower alkyl substituted by fluoro;
R" is hydrogen or lower alkyl;
R''' is lower alkyl, lower alkyl substituted by one or two hydroxy groups, CH(CH$_2$OH)-phenyl, —(CH$_2$)$_2$O-lower alkyl, or phenyl substituted by halogen, or
R" and R''' together with the N-atom to which they are attached form a heterocyclic ring, optionally substituted by one or more lower alkyl, CH$_2$C(O)O-lower alkyl, or CH$_2$C(O)OH;
Ar is a five-membered heteroaryl group;
and pharmaceutically active acid addition salts thereof.

The invention provides all forms of optically pure enantiomers, racemates, or diastereomeric mixtures of the compounds of the invention.

The invention also provides pharmaceutical compositions containing compounds of formula I or pharmaceutically acceptable salts thereof and a pharmaceutically acceptable carrier. The invention further provides methods for the manufacture of the compounds and compositions of the invention.

Compounds of formula I are modulators for amyloid beta and thus, they are useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an", and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "halogen" denotes a chlorine, fluorine, bromine, or iodine, with fluorine being preferred.

The term "lower alkyl substituted by halogen" denotes a lower alkyl group as defined hereinabove which is substituted by one or more, preferably one, two or three halogen atom(s), i.e. chlorine, iodine, fluorine or bromine.

As used herein, the term "lower alkyl substituted by fluoro" denotes an alkyl group as defined above, wherein at least one hydrogen atom is replaced by fluoro, for example $CF_3$, $CHF_2$, $CH_2F$, $CH_2CF_3$, $CH_2CH_2CF_3$, $CH_2CF_2CF_3$, $CH_2CF_2CF_2CF_3$, $CH_2CH_2CF_2CF_3$ and the like.

The term "lower alkyl substituted by hydroxy" denotes a lower alkyl group as defined hereinabove which is substituted by one or more, hydroxy group(s), As used herein, the term "lower alkoxy" denotes a lower alkyl group as defined above that is attached via an oxygen atom.

As used herein, the term "five-membered heteroaryl group" denotes an aromatic ring having five ring atoms, wherein at least two ring atoms are heteroatoms, selected from the group consisting of N, O and S, for example oxazolyl, [1,2,4]triazolyl, imidazol-1-yl, thiazolyl, isothiazolyl, isoxazolyl, pyrazol-1-yl, [1,2,4]-oxadiazol-5-yl or [1,3,4]-oxadiazol-2-yl. Preferred is the imidazolyl group.

The term "heterocyclic ring" denotes a five or six membered non aromatic ring containg a N atom in the 1-position, wherein the remaining ring atoms are selected from N, O and S, for example the groups piperidine-1-yl, morpholinyl, thiomorpholin or piperazine.

"Pharmaceutically acceptable", such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

Preferred compounds are those where Ar is oxazolyl, [1,2,4]triazolyl, imidazol-1-yl, thiazolyl, isothiazolyl, isoxazolyl, pyrazol-1-yl, [1,2,4]-oxadiazol-5-yl or [1,3,4]-oxadiazol-2-yl.

Preferred compounds are those wherein Ar is imidazol-1-yl.

Preferred compounds from this group are those, wherein one of $R^3$ or $R^4$ is NR"R'" and R" and R'" together with the N-atom to which they are attached form a heterocyclic ring, optionally substituted by one or more lower alkyl, $CH_2C(O)$O-lower alkyl or $CH_2C(O)OH$, for example the following compounds:

[3-methoxy-4-(4-methyl-imidazol-1-yl)-phenyl]-(4-methoxy-6-piperidin-1-yl-[1,3,5]triazin-2-yl)-amine;

(1-{4-methoxy-6-[3-methoxy-4-(4-methyl-imidazol-1-yl)-phenylamino]-[1,3,5]triazin-2-yl}-piperidin-4-yl)-acetic acid ethyl ester; and (1-{4-methoxy-6-[3-methoxy-4-(4-methyl-imidazol-1-yl)-phenylamino]-[1,3,5]triazin-2-yl}-piperidin-4-yl)-acetic acid.

Further preferred compounds are those, wherein Ar is imidazol-1-yl and one of $R^3$ or $R^4$ is OR', for example the following compounds

[3-methoxy-4-(4-methyl-imidazol-1-yl)-phenyl]-[4-methoxy-6-(2-trifluoromethyl-phenoxy)-[1,3,5]triazin-2-yl]-amine;

[4-(4-fluoro-phenoxy)-6-methoxy-[1,3,5]triazin-2-yl]-[3-methoxy-4-(4-methyl-imidazol-1-yl)-phenyl]-amine;

[3-methoxy-4-(4-methyl-imidazol-1-yl)-phenyl]-[4-methoxy-6-(3,4,5-trifluoro-phenoxy)-[1,3,5]triazin-2-yl]-amine;

[4-(2,4-dichloro-phenoxy)-6-methoxy-[1,3,5]triazin-2-yl]-[3-methoxy-4-(4-methyl-imidazol-1-yl)-phenyl]-amine;

[4-(2-chloro-pyridin-3-yloxy)-6-methoxy-[1,3,5]triazin-2-yl]-[3-methoxy-4-(4-methyl-imidazol-1-yl)-phenyl]-amine;

[4-isopropoxy-6-(2-trifluoromethyl-phenoxy)-[1,3,5]triazin-2-yl]-[3-methoxy-4-(4-methyl-imidazol-1-yl)-phenyl]-amine;

(4,6-diisopropoxy-[1,3,5]triazin-2-yl)-[3-methoxy-4-(4-methyl-imidazol-1-yl)-phenyl]-amine;

[4,6-bis-(2-trifluoromethyl-phenoxy)-[1,3,5]triazin-2-yl]-[3-methoxy-4-(4-methyl-imidazol-1-yl)-phenyl]-amine; and

[4-(4-chloro-benzyloxy)-6-methoxy-[1,3,5]triazin-2-yl]-[3-methoxy-4-(4-methyl-imidazol-1-yl)-phenyl]-amine.

Further preferred compounds are those, wherein Ar is imidazol-1-yl and one of $R^3$ or $R^4$ is NR"R'" and R" is H or lower alkyl and R'" is lower alkyl, lower alkyl substituted by one or two hydroxy groups, —$(CH_2)_2OCH_3$, or phenyl substituted by halogen, for example the following compounds N-(4-chloro-phenyl)-6-methoxy-N'-[3-methoxy-4-(4-methyl-imidazol-1-yl)-phenyl]-[1,3,5]triazine-2,4-diamine;

N-(4-chloro-phenyl)-6-methoxy-N'-[3-methoxy-4-(4-methyl-imidazol-1-yl)-phenyl]-N-methyl-[1,3,5]triazine-2,4-diamine;

N-(4-chloro-phenyl)-N'-[3-methoxy-4-(4-methyl-imidazol-1-yl)-phenyl]-N-methyl-[1,3,5]triazine-2,4-diamine; and N-(4-chloro-phenyl)-6-isopropoxy-N'-[3-methoxy-4-(4-methyl-imidazol-1-yl)-phenyl]-N-methyl-[1,3,5]triazine-2,4-diamine.

Preferred compounds are those where one of $R^3$ and $R^4$ is halogen.

Also preferred are compounds where one of $R^3$ and $R^4$ is lower alkyl.

Further preferred are compounds where one of $R^3$ and $R^4$ is C(O)O-lower alkyl.

Preferred compounds are those where one of $R^3$ and $R^4$ is OR'.

Other preferred compounds are those where one of $R^3$ and $R^4$ is NR"R'".

Still other preferred compounds are those where one of $R^3$ and $R^4$ is lower alkyl substituted by halogen or hydroxyl.

Further, preferred compounds are those where one of $R^3$ and $R^4$ is phenyl optionally substituted by one or two halogen atoms.

Preferred compounds are those where one of $R^3$ and $R^4$ is benzyl optionally substituted by one or two halogen atoms.

The present compounds of formula I and their pharmaceutically acceptable salts can be prepared by methods known in the art, for example, by processes described below, which process comprises a) reacting a compound of formula

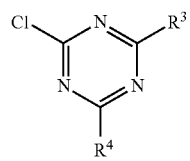

with a compound of formula

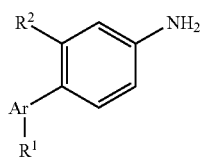

to obtain a compound of formula

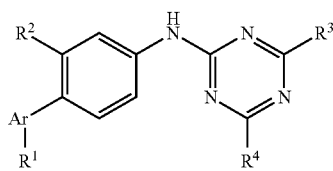

I wherein the substituents are as defined above, or b) reacting a compound of formula

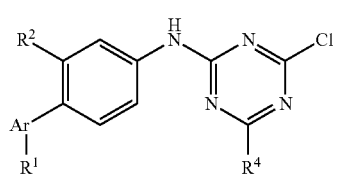

VI with a compound of formula
R³H to obtain a compound of formula

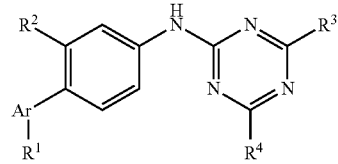

I wherein the substituents are as defined above, or c) reacting a compound of formula

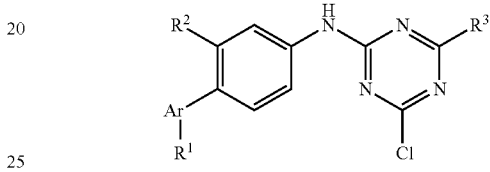

V with a compound of formula
R⁴H to obtain a compound of formula

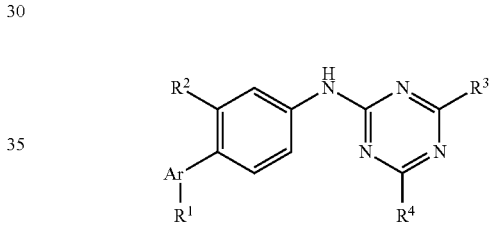

I and, if desired, converting the compounds obtained into pharmaceutically acceptable acid addition salts.

The compounds of formula I can be prepared in accordance with process variant a), b) or c) and with the following schemes 1, 2 and 3.

The present compounds of formula I and their pharmaceutically acceptable salts can be prepared by methods known in the art, starting either from cyanuric chloride II (commercial available) or from commercially available dichloro-intermediates by sequential substitution of the chloro-atoms, as shown in the Schemes 1 and 2.

Overview scheme 1

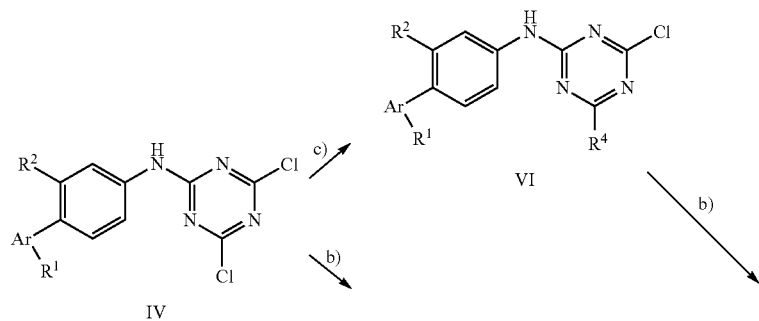

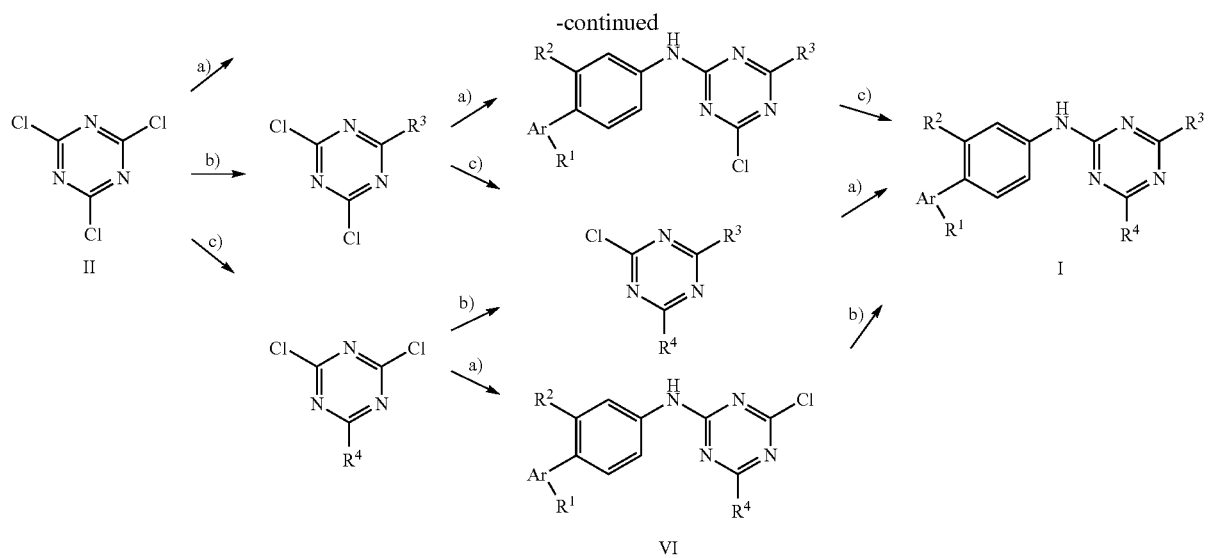

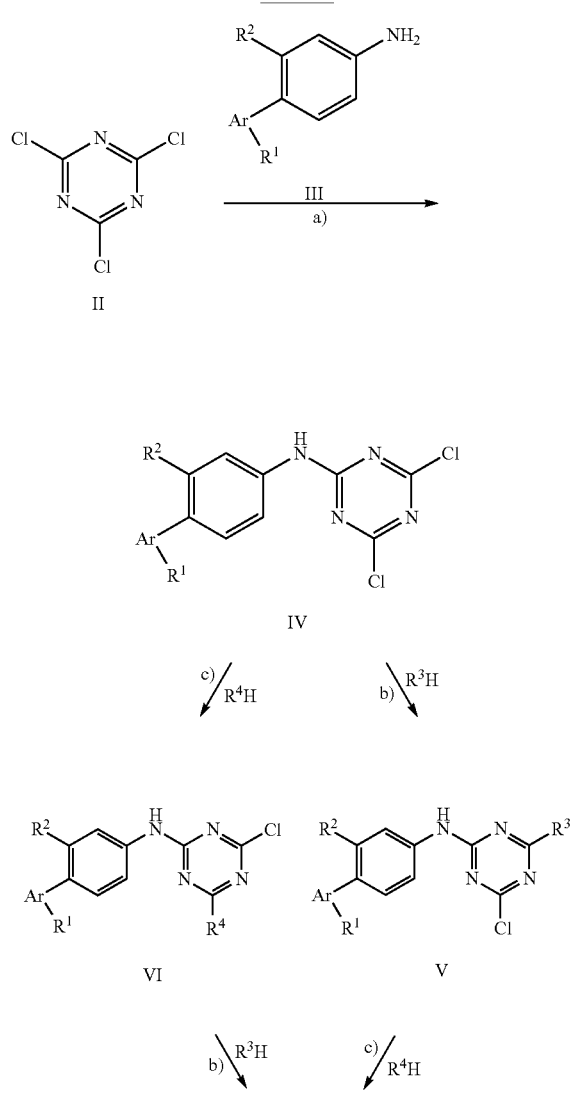

When $R^3$ or $R^4$ is hydrogen, the replacement of the chloro atom can be done by reduction with Pd on charcoal and hydrogen, as described for example in J. Am. Chem. Soc. 78, 2477 (1956).

When $R^3$ or $R^4$ is lower alkyl, the replacement of the chloro atom can be done with alkyl-Grignard reagents, as described for example in Helv. 33, 1365 (1950).

When $R^3$ or $R^4$ is OR', the nucleophilic substitution of the chloro atom can be done by reaction with the corresponding alcohols or alcoholates, in analogy to J. Am. Chem. Soc. 79, 944 (1957) or the corresponding phenolates, in analogy to J. Am. Chem. Soc. 73, 2990 (1951).

When $R^3$ or $R^4$ is NR"R'" then the nucleophilic substitution of the chloro atom can be done with the corresponding amine HNR"R'", as shown for example in Bull. Soc. Chim. Fr. 1973, 2112. Alternatively, for less nucleophilic or sterically hindered amines, the substitution can be done under Buchwald-Hartwig conditions, using Pd-catalysis.

When $R^3$ is phenyl or substituted phenyl, the chloro atom can be reacted with arylboronic acids in presence of a base and a palladium catalyst (Suzuki-coupling, as described, for example, in Tetrahedron 57, 2787 (2001)) for other triazine-derivatives.

When $R^3$ is lower alkyl substituted by hydroxy, for example the group $C(CH_3)_2OH$, the chloro atom can be alkoxycarbonylated, as described, for example, in Tetrahedron 55, 405 (1995) for analogous pyrimidine-derivatives. The resulting ester is then reacted with methylmagnesium halide, as described, for example, in Tetrahedron 61, 6330 (2005) for analogous pyridine-derivatives. This procedure is shown in Scheme 3.

Scheme 3

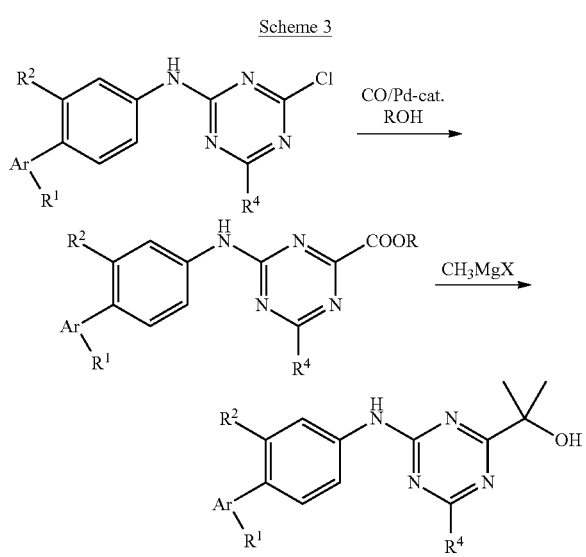

Aniline III can be prepared as described in Scheme 4.

Scheme 4

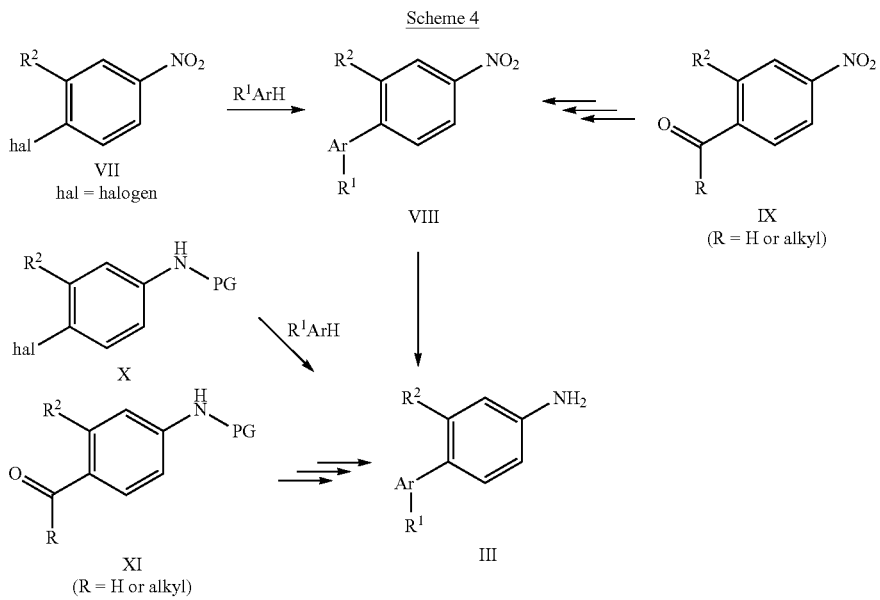

Nucleophilic substitution at room temperature or elevated temperature (e.g reflux or under pressure using a microwave oven) under neutral conditions or in the presence of a base (like e.g. potassium carbonate), neat or in a polar solvent (like e.g. THF or DMSO etc.) of a substituted 4-nitro-phenyl halide VII (hal=F, Cl, Br, I) with a compound R'H, (like 4-methylimidazole) yields a nitro derivative VIII. Alternatively, a nitro derivative VIII can be prepared from a suitable precursor, such as a carbonyl derivative IX (R=H or $C_{1-4}$-alkyl), by applying standard reaction sequences for the formation of the substituent R'. A nitro compound VIII can be reduced to an aniline III using generally known procedures, e.g. hydrogenation in the presence of a catalyst (like e.g. 10% palladium on carbon) in a solvent (like e.g. ethanol or ethyl acetate) or, by using a metal (like e.g. iron) or a metal salt (like e.g. stannous chloride) in a polar solvent (like e.g. acetic acid or tetrahydrofuran). Alternatively, aniline III can be prepared by introducing a substituent $R^1$ into a N-protected aniline derivative X (PG=protecting group) using generally known procedures, e.g. displacement reactions under catalytic conditions (like e.g. palladium(0) or copper(II) catalysis) or, by forming a group $R^1$ in a N-protected aniline derivative XI, respectively, and subsequently cleaving off the protecting group.

The compounds were investigated in accordance with the test given hereinafter.

Cellular Assay

Human neuroglioma H4 cells overexpressing human APP were plated at 30,000 cells/well/200 µl in 96-well plates in IMDM media containing 10% FCS, 0.2 mg/l Hygromycin B and incubated for 2 h at 37° C., 5% $CO_2$ prior to adding test compounds.

Compounds for testing were dissolved in 100% $Me_2SO$ yielding in a 10 mM stock solution. Typically 12 µl of these solutions were further diluted in 1000 µl of IMDM media (w/o FCS,). Sub sequential 1:1 dilutions gave a ten point dose response curve. 100 µl of each dilution was added to the cells in 96-well plates. Appropriate controls using vehicle only and reference compound were applied to this assay. The final concentration of $Me_2SO$ was 0.4%. After incubation for 22 hrs at 37° C., 5% $CO_2$, 50 µl supernatant was transferred into round-bottom 96-well polypropylene plates for detection of Aβ42. 50 µl assay buffer (50 mM Tris/C1, pH 7.4, 60 mM NaCl, 0.5% BSA, 1% TWEEN 20) was added to the wells followed by the addition of 100 µl of detection antibody (ruthenylated Aβ42-specific antibody BAP15 0.0625 µg/mL in assay buffer). 50 µl of a premix of capture antibody (biotinylated 6E10 antibody, 1 µg/mL) and Steptavidin-coated magnetic beads (Dynal M-280, 0.125 mg/mL) were preincubated for 1 hr at room temperature before adding the assay plates. Assay plates were incubated on a shaker for 3 hrs at room temperature and finally read in the Bioveris M8 Analyser according to the manufacturer's instructions (Bioveris).

Toxicity of compounds was monitored by a cell viability test of the compound-treated cells using a colorimetric assay (CellTiter 96™ AQ assay, Promega) according to the manufacturer's instructions. Briefly, after removal of 50 µl cell culture supernatant for detection of Aβ42, 20 μl of 1× MTS/PES solution was added to the cells and incubated for 30 min at 37° C., 5% $CO_2$. Optical density was then recorded at 490 nm.

$IC_{50}$ values for inhibition of Aβ42 secretion were calculated by nonlinear regression fit analysis using XLfit 4.0 software (IDBS).

The preferred compounds show a $IC_{50}$<1.0 (μM). In the list below are described data of γ-secretase inhibition for some compounds of the invention:

| Example No. | $IC_{50}$ in vitro (μM) |
| --- | --- |
| 2 | 0.19 |
| 3 | 0.38 |
| 4 | 0.87 |
| 5 | 0.25 |
| 6 | 0.95 |
| 7 | 0.70 |
| 9 | 0.45 |
| 11 | 0.32 |
| 13 | 0.20 |
| 16 | 0.23 |
| 17 | 0.12 |
| 19 | 0.91 |
| 21 | 0.93 |
| 23 | 0.16 |
| 25 | 0.72 |
| 26 | 0.59 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of the γ-secretase, such as of Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| | | Tablet Formulation (Wet Granulation) mg/tablet | | | |
| --- | --- | --- | --- | --- | --- |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
| --- | --- | --- | --- | --- | --- |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLE 1

(4,6-Dimethoxy-[1,3,5]triazin-2-yl)-[3-methoxy-4-(4-methyl-imidazol-1-yl)-phenyl]-amine

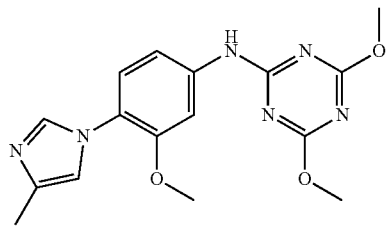 [SMILES: COc1nc(Nc2ccc(-n3cnc(C)c3)c(OC)c2)nc(OC)n1]

a) 1-(2-Methoxy-4-nitro-phenyl)-4-methyl-1H-imidazole

A solution of 2-chloro-5-nitroanisole (187 mg, 1 mmol), of 4-methyl-1H-imidazole (335 mg, 4 mmol) and of potassium hydroxide (99 mg, 1.5 mmol) in DMSO (0.86 mL) was stirred for 5 h at 80° C. under an atmosphere of nitrogen. After cooling to 20° C. the reaction was poured onto ice-water. A precipitation was formed and the suspension was stirred for 15 min. The solid was filtered off, washed with water, dissolved in dichloromethane, dried over sodium sulfate, filtered and the solvent was evaporated under reduced pressure to yield a yellow solid. The crude product was purified on silica gel using dichloromethane/methanol (19:1 v/v) as eluent to yield the title compound (106 mg, 45%) as a pale-yellow solid. Alternatively the product can be also crystallized from the crude material from diethyl ether.

MS ISP (m/e): 234.3 (100) [(M+H)+].

$^1$H NMR (CDCl$_3$, 300 MHz): δ (ppm)=7.97 (d, 1H), 7.96 (s, 1H), 7.83 (s, 1H), 7.42 (d, 1H), 7.00 (s, 1H), 4.00 (s, 3H), 2.31 (s, 3H).

b) 3-Methoxy-4-(4-methyl-imidazol-1-yl)-phenylamine 1-(2-Methoxy-4-nitro-phenyl)-4-methyl-1H-imidazole (2.52 g, 10.8 mmol) dissolved in ethanol (110 mL) was stirred under an atmosphere of hydrogen at 20° C. for 3.5 h in the presence of 10% palladium on charcoal (0.25 g). The catalyst was filtered off and washed with ethanol. The solvent of the filtrate was evaporated under reduced pressure. The crude product was purified on silica gel using dichloromethane/methanol (19:1 v/v) as eluent. The fraction containing the product was suspended in diethyl ether, stirred for 15 min, filtered and dried to yield the title compound (1.72 g, 78%) as a yellow solid.

MS ISP (m/e): 204.3 (100) [(M+H)+].

$^1$H NMR (CDCl$_3$, 300 MHz): δ (ppm)=7.48 (s, 1H), 6.91 (d, 1H), 6.88 (s, 1H), 6.35 (s, 1H), 6.17 (d, 1H), 3.68 (s, 3H), 2.11 (s, 3H).

c) (4,6-Dimethoxy-[1,3,5]triazin-2-yl)-[3-methoxy-4-(4-methyl-imidazol-1-yl)-phenyl]-amine Palladium acetate (5.0 mg, 0.022 mmol) and (2-biphenylyl) dicyclohexylphosphine (16 mg, 0.046 mmol) were dissolved under an atmosphere of argon in dioxane (2 mL) and stirred for 10 min at 20° C. This solution was added at 20° C. under an atmosphere of nitrogen to a flask containing 3-methoxy-4-(4-methyl-imidazol-1-yl)-phenylamine (116 mg, 0.57 mmol), 2-chloro-4,6-dimethoxy-1,3,5-triazine (100 mg, 0.57 mmol) and potassium carbonate (1.57 g, 11.4 mmol) in 3 ml of dioxane. The resulting mixture was refluxed over night under argon, poured into a saturated aqueous solution of sodium chloride and extracted 3 times with ethyl acetate. The organic layer was dried, evaporated and the residue purified by column chromatography on silica gel using dichloromethane/methanol (98:2 v/v) as eluent to yield the title compound (18 mg, 9%) as a yellowish solid.

MS ISP (m/e): 343.0 (100) [(M+H)+].

$^1$H NMR (DMSO-D$_6$, 300 MHz): δ (ppm)=10.31 (s broad, 1H), 7.85 (s, 1H), 7.30 (s, 2H), 7.06 (s, 1H), 3.94 (s broad, 6H), 3.80 (s, 3H), 2.14 (s, 3H).

EXAMPLE 2

N-(4-Chloro-phenyl)-6-methoxy-N'-[3-methoxy-4-(4-methyl-imidazol-1-yl)-phenyl]-[1,3,5]triazine-2,4-diamine

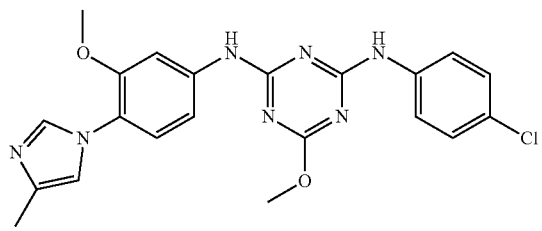 [SMILES: COc1nc(Nc2ccc(Cl)cc2)nc(Nc2ccc(-n3cnc(C)c3)c(OC)c2)n1]

a) (4-Chloro-6-methoxy-[1,3,5]triazin-2-yl)-[3-methoxy-4-(4-methyl-imidazol-1-yl)-phenyl]-amine Triethylamine (0.23 ml, 1.62 mmol) was added to a solution of 3-methoxy-4-(4-methyl-imidazol-1-yl)-phenylamine (300 mg, 1.48 mmol) in 5 ml of methanol. The mixture was cooled in an ice-bath and 2,4-dichloro-6-methoxy-[1,3,5]triazine (266 mg, 1.48 mmol) added portionwise. The mixture was stirred for 1 hour at 0° C. The resulting precipitate was removed by filtration and dried to give the title compound as a slightly brownish solid (317 mg, 62%).

MS ISP (m/e): 345.3 (100) & 347.2 (40) [(M+H)+].

$^1$H NMR (DMSO-D$_6$, 300 MHz): δ (ppm)=10.85 (s broad, 1H), 7.78 (s broad, 1H), 7.71 (s, 1H), 7.45-7.20 (m, 2H), 7.09 (s, 1H), 4.00 (s broad, 3H), 3.82 (s, 3H), 2.16 (s, 3H).

b) N-(4-Chloro-phenyl)-6-methoxy-N'-[3-methoxy-4-(4-methyl-imidazol-1-yl)-phenyl]-[1,3,5]-triazine-2,4-diamine The title compound was prepared from (4-chloro-6-methoxy-[1,3,5]triazin-2-yl)-[3-methoxy-4-(4-methyl-imidazol-1-yl)-phenyl]-amine and 4-chloroaniline in analogy to example 1c). It was obtained in 15% yield as a colorless solid.

MS ISP (m/e): 438.2 (100) & 440.3 (37) [(M+H)+].

¹H NMR (CDCl₃, 300 MHz): δ (ppm)=7.66 (s, 1H), 7.53 (d, 2H), 7.46 (s broad, 1H), 7.35-7.05 (m, 6H), 6.88 (s, 1H), 4.01 (s, 3H), 3.38 (s broad, 3H), 2.30 (s, 3H).

EXAMPLE 3

[3-Methoxy-4-(4-methyl-imidazol-1-yl)-phenyl]-[4-methoxy-6-(2-trifluoromethyl-phenoxy)-[1,3,5]triazin-2-yl]-amine

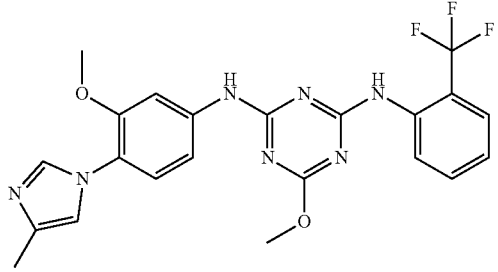 [SMILES: COc1nc(Nc2ccc(-n3cnc(C)c3)c(OC)c2)nc(Nc2ccccc2C(F)(F)F)n1]

A mixture of (4-chloro-6-methoxy-[1,3,5]triazin-2-yl)-[₃-methoxy-4-(4-methyl-imidazol-1-yl)-phenyl]-amine (70 mg, 0.2 mmol), 2-hydroxybenzotrifluoride (34 mg, 0.21 mmol) and potassium carbonate (31 mg, 0.22 mmol) in 5 ml acetonitrile was refluxed overnight. Water was added to the mixture. The product was extracted with ethylacetate, concentrated and purified by trituration with diethyl ether to give the title compound as colorless solid (43 mg, 45%).

MS ISP (m/e): 473.2 (100) [(M+H)⁺].

¹H NMR (CDCl₃, 300 MHz): δ (ppm)=7.72 (d, 1H), 7.62 (t, 2H), 7.50 (s broad, 1H), 7.39 (t, 1H), 7.35-7.25 (m, 2H), 7.10 (s broad, 1H), 6.85 (s broad, 1H), 4.00 (s, 3H), 3.85 & 3.05 (two s, total 3H), 2.29 (s, 3H).

EXAMPLE 4

[4-(4-Fluoro-phenoxy)-6-methoxy-[1,3,5]triazin-2-yl]-[3-methoxy-4-(4-methyl-imidazol-1-yl)-phenyl]-amine

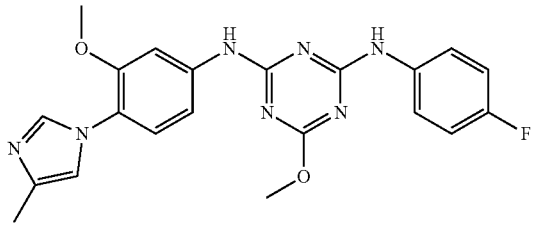 [SMILES: COc1nc(Nc2ccc(F)cc2)nc(Nc2ccc(-n3cnc(C)c3)c(OC)c2)n1]

The title compound was prepared from (4-chloro-6-methoxy-[1,3,5]triazin-2-yl)-[3-methoxy-4-(4-methyl-imidazol-1-yl)-phenyl]-amine and 4-fluorophenol in analogy to example 3. It was purified by column chromatography on silica gel using ethyl acetate as eluent to give the title compound as a yellowish solid in 52% yield.

MS ISP (m/e): 421.4 (100) [(M+H)⁺].

¹H NMR (CDCl₃, 300 MHz): δ (ppm)=7.62 (s, 1H), 7.55-6.90 (m, 8H), 4.00 (s, 3H), 3.70 (s broad, 3H), 2.30 (s, 3H).

EXAMPLE 5

N-(4-Chloro-phenyl)-6-methoxy-N'-[3-methoxy-4-(4-methyl-imidazol-1-yl)-phenyl]-N-methyl-[1,3,5]triazine-2,4-diamine

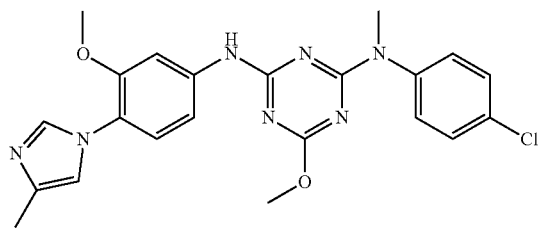 [SMILES: COc1nc(Nc2ccc(-n3cnc(C)c3)c(OC)c2)nc(N(C)c2ccc(Cl)cc2)n1]

This compound was prepared from (4-chloro-6-methoxy-[1,3,5]triazin-2-yl)-[3-methoxy-4-(4-methyl-imidazol-1-yl)-phenyl]-amine and 4-chloro-N-methylaniline in analogy to example 1c. It was purified by column chromatography on Si—NH2 gel (Isolute) using ethyl acetate as eluent to give the title compound as a colorless solid in 14% yield.

MS ISP (m/e): 452.2 (100) & 454.2 (39)[(M+H)⁺].

¹H NMR (CDCl₃, 300 MHz): δ (ppm)=7.62 (s, 1H), 7.38 (d, 2H), 7.30-6.80 (m, 6H), 6.85 (s, 1H), 3.95 (s broad, 3H), 3.65 (s broad, 3H), 3.51 (s, 3H), 2.30 (s, 3H).

EXAMPLE 6

[3-Methoxy-4-(4-methyl-imidazol-1-yl)-phenyl]-[4-methoxy-6-(3,4,5-trifluoro-phenoxy)-[1,3,5]triazin-2-yl]-amine

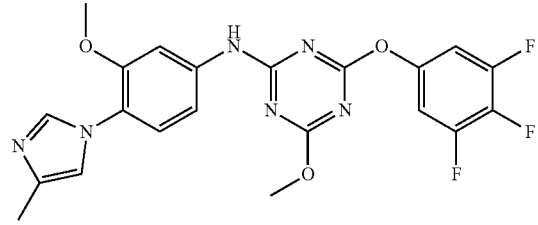 [SMILES: COc1nc(Nc2ccc(-n3cnc(C)c3)c(OC)c2)nc(Oc2cc(F)c(F)c(F)c2)n1]

This compound was prepared from (4-chloro-6-methoxy-[1,3,5]triazin-2-yl)-[₃-methoxy-4-(4-methyl-imidazol-1-yl)-phenyl]-amine and 3,4,5-trifluorophenol in analogy to example 3. Chromatography on silica gel using ethyl acetate as an eluent gave the title compound as a colorless solid in 25% yield.

MS ISP (m/e): 457.5 (100) [(M+H)⁺].

¹H NMR (CDCl₃, 300 MHz): δ (ppm)=7.64 (s, 1H), 7.55-6.85 (m, 6H), 4.02 (s, 3H), 3.71 (s broad, 3H), 3.51 (s, 3H), 2.30 (s, 3H).

EXAMPLE 7

[3-Methoxy-4-(4-methyl-imidazol-1-yl)-phenyl]-(4-methoxy-6-piperidin-1-yl-[1,3,5]triazin-2-yl)-amine

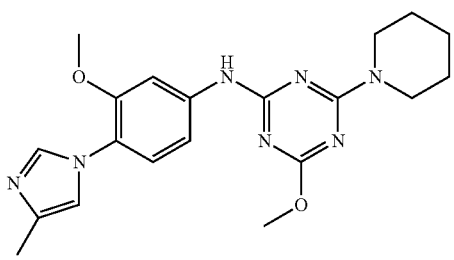 [SMILES: COc1nc(Nc2ccc(-n3cnc(C)c3)c(OC)c2)nc(N2CCCCC2)n1]

This compound was prepared from (4-chloro-6-methoxy-[1,3,5]triazin-2-yl)-[₃-methoxy-4-(4-methyl-imidazol-1-yl)-phenyl]-amine and piperidine in analogy to example 1c. Chromatography on Si—NH2 gel (Isolute) using ethyl acetate as an eluent gave the title compound as a colorless solid in 22% yield.

MS ISP (m/e): 396.1 (100) [(M+H)⁺].

¹H NMR (CDCl₃, 300 MHz): δ (ppm)=7.72 (s, 1H), 7.63 (s, 1H), 7.17 (d, 1H), 6.97 (d, 1H), 6.94 (s, 1H), 6.87 (s, 1H), 3.94 (s, 3H), 3.85 (s, 3H), 3.81 (t broad, 4H), 2.30 (s, 3H), 1.75-1.65 (m 2H), 1.65-1.55 (m, 4H).

EXAMPLE 8

6-Chloro-N-[3-methoxy-4-(4-methyl-imidazol-1-yl)-phenyl]-N,N'-dimethyl-[1,3,5]triazine-2,4-diamine

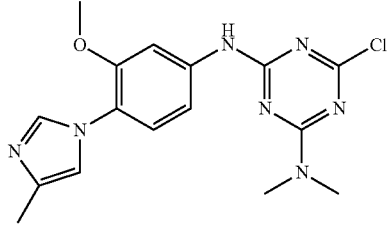 [SMILES: COc1cc(Nc2nc(Cl)nc(N(C)C)n2)ccc1-n1cnc(C)c1]

(4-Chloro-6-methoxy-[1,3,5]triazin-2-yl)-[3-methoxy-4-(4-methyl-imidazol-1-yl)-phenyl]-amine (800 mg, 3.94 mmol) was dissolved in 10 ml of methanol and cooled in an ice-bath. Triethylamine (0.6 ml, 4.33 mmol) was added, followed by (4,6-dichloro-[1,3,5]triazin-2-yl)-dimethyl-amine (760 mg, 3.94 mmol; Chem. Pharm. Bull. 45, 291 (1997)). The resulting slurry was stirred for 1 hour at 0° C. and filtered, to give the title compound as a slightly brownish solid in 57% yield.

MS ISP (m/e): 360.2 (100) & 362.3 (46) [(M+H)⁺].

¹H NMR (DMSO-D₆, 300 MHz): δ (ppm)=10.22 (s broad, 1H), 7.90 (s broad, 1H), 7.68 (s, 1H), 7.35-7.15 (m, 2H), 7.06 (s, 1H), 3.70 (s, 3H), 3.20 (s, 3H), 3.13 (s, 3H), 2.13 (s, 3H).

EXAMPLE 9

[4-(2,4-Dichloro-phenoxy)-6-methoxy-[1,3,5]triazin-2-yl]-[3-methoxy-4-(4-methyl-imidazol-1-yl)-phenyl]-amine

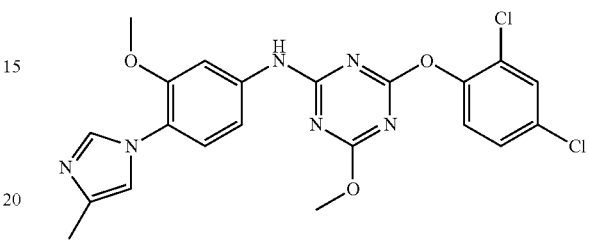

This compound was prepared from (4-chloro-6-methoxy-[1,3,5]triazin-2-yl)-[₃-methoxy-4-(4-methyl-imidazol-1-yl)-phenyl]-amine and 2,4-dichlorophenol in analogy to example 3. Chromatography on silica gel using ethyl acetate as an eluent gave the title compound as a colorless solid in 81% yield.

MS ISN (m/e): 471.4 (100) [(M−H)⁻].

¹H NMR (CDCl₃, 300 MHz): δ (ppm)=7.62 (s, 1H), 7.48 (d, 1H), 7.40-7.10 (m, 4H), 6.88 (s, 1H), 4.01 (s, 3H), 3.75 (s broad, 3H), 2.30 (s, 3H).

EXAMPLE 10

[3-Methoxy-4-(4-methyl-imidazol-1-yl)-phenyl]-[4-(2-trifluoromethyl-phenoxy)-[1,3,5]triazin-2-yl]-amine

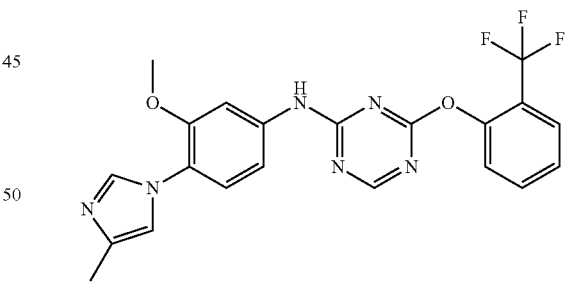

a) (4-Chloro-[1,3,5]triazin-2-yl)-[3-methoxy-4-(4-methyl-imidazol-1-yl)-phenyl]-amine This compound was prepared from 3-methoxy-4-(4-methyl-imidazol-1-yl)-phenylamine and 2,4-dichloro-1,3,5-triazine in analogy to example 2a. The compound precipitated from methanol in 50% yield.

MS ISP (m/e): 317.1 (100) & 319.2 (38) [(M+H)⁺].

¹H NMR (DMSO-D₆, 300 MHz): δ (ppm)=10.90 (s, 1H), 8.68 (s broad, 1H), 7.73 (s, 1H), 7.60 (s, 1H), 7.36 (s, 1H), 7.09 (s, 1H), 3.81 (s, 3H), 2.15 (s, 3H).

b) [3-Methoxy-4-(4-methyl-imidazol-1-yl)-phenyl]-[4-(2-trifluoromethyl-phenoxy)-[1,3,5]-triazin-2-yl]-amine This compound was prepared from (4-chloro-[1,3,5]triazin-2-yl)-[3-methoxy-4-(4-methyl-imidazol-1-yl)-phenyl]-amine and 2-hydroxybenzotrifluoride in analogy to example 3. Chromatography on silica gel using ethyl acetate as an eluent gave the title compound as a colorless solid in 33% yield.

MS ISN (m/e): 441.4 (100) [(M−H)⁻].

$^1$H NMR (CDCl$_3$, 300 MHz): δ (ppm)=8.57 (s broad, 1H), 7.74 (d, 1H), 7.70-6.90 (m, 8H), 6.86 (s, 1H), 3.75 and 3.13 (two broad s, total 3H), 2.29 (s, 3H)

EXAMPLE 11

N-(4-Chloro-phenyl)-N'-[3-methoxy-4-(4-methyl-imidazol-1-yl)-phenyl]-N-methyl-[1,3,5]triazine-2,4-diamine

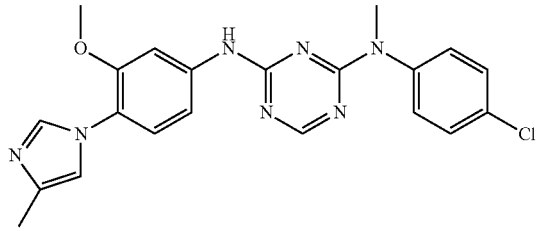 [SMILES: COc1cc(Nc2ncnc(N(C)c3ccc(Cl)cc3)n2)ccc1-n1cnc(C)c1]

This compound was prepared from (4-chloro-[1,3,5]triazin-2-yl)-[3-methoxy-4-(4-methyl-imidazol-1-yl)-phenyl]-amine and 4-chloro-N-methylaniline in analogy to example 1c. Chromatography on Si—NH2 gel (Isolute) using ethyl acetate as an eluent gave the title compound as a colorless solid in 23% yield.

MS ISN (m/e): 420.3 (100) & 422.4 (29) [(M−H)⁻].

$^1$H NMR (CDCl$_3$, 300 MHz): δ (ppm)=8.32 (s broad, 1H), 7.62 (s, 1H), 7.40 (d, 2H), 7.28 (d, 2H), 7.12 (s broad, 2H), 7.00 (s broad, 1H), 6.86 (s, 1H), 3.72 (s broad, 3H), 3.53 (s, 3H)

EXAMPLE 12

[3-Methoxy-4-(4-methyl-imidazol-1-yl)-phenyl]-[4-methoxy-6-(pyridin-3-yloxy)-[1,3,5]triazin-2-yl]-amine

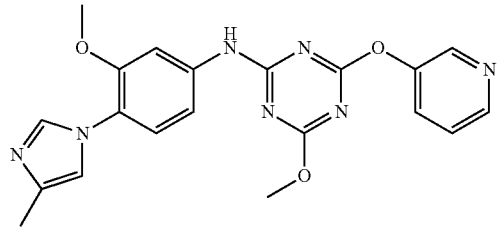 [SMILES: COc1nc(Nc2ccc(-n3cnc(C)c3)c(OC)c2)nc(Oc2cccnc2)n1]

The title compound was prepared from (4-chloro-6-methoxy-[1,3,5]triazin-2-yl)-[3-methoxy-4-(4-methyl-imidazol-1-yl)-phenyl]-amine and 3-hydroxypyridine in analogy to example 3. It was purified by column chromatography on Si—NH2 gel (Isolute) using ethyl acetate as eluent to give the title compound as a yellowish solid in 21% yield.

MS ISN (m/e): 404.6 (100) [(M−H)⁻].

$^1$H NMR (CDCl$_3$, 300 MHz): δ (ppm)=8.57 (d, 1H), 8.53 (dxd, 1H), 7.65-7.50 (m, 2H), 7.40-7.30 (m, 2H), 7.25-6.90 (m, 2H), 6.86 (s, 2H), 4.01 (s, 3H), 3.73 & 3.62 (two broad s, total 3H), 2.29 (s, 3H).

EXAMPLE 13

[4-(2-Chloro-pyridin-3-yloxy)-6-methoxy-[1,3,5]triazin-2-yl]-[3-methoxy-4-(4-methyl-imidazol-1-yl)-phenyl]-amine

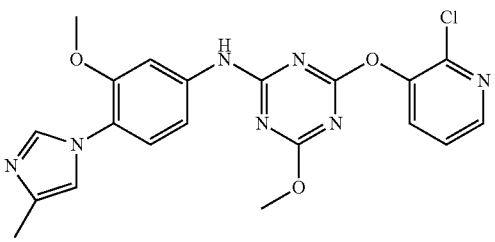 [SMILES: COc1nc(Nc2ccc(-n3cnc(C)c3)c(OC)c2)nc(Oc2cccnc2Cl)n1]

The title compound was prepared from (4-chloro-6-methoxy-[1,3,5]triazin-2-yl)-[3-methoxy-4-(4-methyl-imidazol-1-yl)-phenyl]-amine and 2-chloro-3-hydroxypyridine in analogy to example 3. It was purified by column chromatography on Si—NH2 gel (Isolute) using ethyl acetate as eluent to give the title compound as a yellowish solid in 76% yield.

MS ISN (m/e): 484.6 (100) [(M−H)⁻].

$^1$H NMR (CDCl$_3$, 300 MHz): δ (ppm)=7.75-7.50 (m, 3H), 7.40-6.80 (m, 5H), 3.87 & 3.73 (two s, total 3H), 3.27 & 3.22 (two s, total 3H), 2.30 (s, 3H).

EXAMPLE 14

[3-Methoxy-4-(4-methyl-imidazol-1-yl)-phenyl]-[4-methoxy-6-(2-methyl-pyridin-3-yloxy)-[1,3,5]triazin-2-yl]-amine

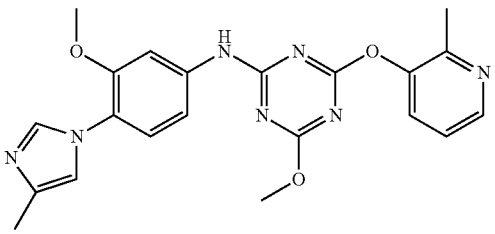 [SMILES: COc1nc(Nc2ccc(-n3cnc(C)c3)c(OC)c2)nc(Oc2cccnc2C)n1]

The title compound was prepared from (4-chloro-6-methoxy-[1,3,5]triazin-2-yl)-[3-methoxy-4-(4-methyl-imidazol-1-yl)-phenyl]-amine and 3-hydroxy-2-methylpyridine in analogy to example 3. It was purified by column chromatography on Si—NH2 gel (Isolute) using ethyl acetate as eluent to give the title compound as a yellowish solid in 34% yield.

MS ISP (m/e): 420.2 (100) [(M+H)⁺].

¹H NMR (CDCl₃, 300 MHz): δ (ppm)=8.44 (d, 1H), 7.62 (s, 1H), 7.44 (d, 1H), 7.35-7.05 (m, 4H), 6.85 (s, 1H), 4.01 (s, 3H), 3.83 & 3.58 (two broad s, total 3H), 2.48 (s, 3H), 2.29 (s, 3H).

EXAMPLE 15

[4-((2S,6R)-2,6-Dimethyl-morpholin-4-yl)-6-methoxy-[1,3,5]triazin-2-yl]-[3-methoxy-4-(4-methyl-imidazol-1-yl)-phenyl]-amine

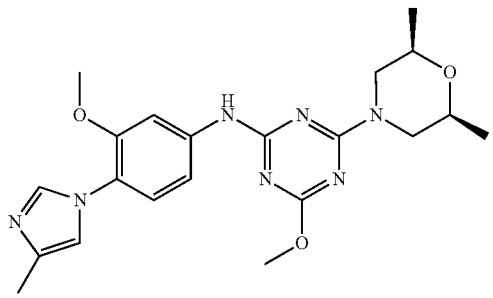 [SMILES: COc1nc(Nc2ccc(-n3cnc(C)c3)c(OC)c2)nc(N2C[C@@H](C)O[C@@H](C)C2)n1]

The title compound was prepared from (4-chloro-6-methoxy-[1,3,5]triazin-2-yl)-[3-methoxy-4-(4-methyl-imidazol-1-yl)-phenyl]-amine and cis-2,6-dimethylmorpholine in analogy to example 1c. It was purified by column chromatography on Si—NH2 gel (Isolute) using ethyl acetate as eluent to give the title compound as a yellowish solid in 58% yield.

MS ISP (m/e): 426.3 (100) [(M+H)⁺]

¹H NMR (CDCl₃, 300 MHz): δ (ppm)=7.68 (s, 1H), 7.63 (s, 1H), 7.17 (d, 1H), 7.00-6.90 (m, 2H), 6.87 (s, 1H), 4.60 (d broad, 2H), 3.96 (s, 3H), 3.86 (s, 3H), 3.70-3.50 (m, 2H), 2.62 (t broad, 2H), 2.30 (s, 3H), 1.24 (d, 6H).

EXAMPLE 16

[4-Isopropoxy-6-(2-trifluoromethyl-phenoxy)-[1,3,5]triazin-2-yl]-[3-methoxy-4-(4-methyl-imidazol-1-yl)-phenyl]-amine

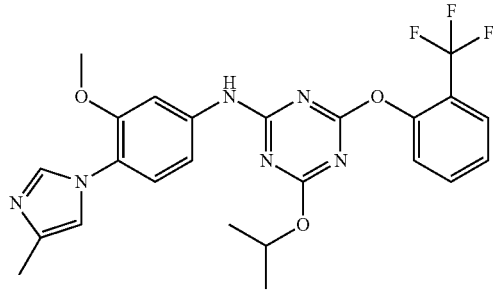 [SMILES: COc1cc(Nc2nc(Oc3ccccc3C(F)(F)F)nc(OC(C)C)n2)ccc1-n1cnc(C)c1]

a) (4-Chloro-6-isopropoxy-[1,3,5]triazin-2-yl)-[3-methoxy-4-(4-methyl-imidazol-1-yl)-phenyl]-amine The title compound was prepared from 3-methoxy-4-(4-methyl-imidazol-1-yl)-phenylamine and 2,4-dichloro-6-isopropoxy-[1,3,5]triazine (Synth. Commun. 24, 2153 (1994)) in analogy to example 2a. The compound crystallized from methanol as a slightly brownish solid in 41% yield.

MS ISN (m/e): 373.3 (100) & 375.4 (33) [(M−H)⁻].

¹H NMR (DMSO-D₆, 300 MHz): δ (ppm)=10.78 (s broad, 1H), 7.71 (s, 1H), 7.63 (s broad, 1H), 7.40-7.20 (m, 2H), 7.08 (s, 1H), 5.28 (sept, 1H), 3.80 (s, 3H), 2.15 (s, 3H), 1.35 (d, 6H).

b)[4-Isopropoxy-6-(2-trifluoromethyl-phenoxy)-[1,3,5]-triazin-2-yl]-[3-methoxy-4-(4-methyl-imidazol-1-yl)-phenyl]-amine This compound was prepared from (4-chloro-6-isopropoxy-[1,3,5]triazin-2-yl)-[₃-methoxy-4-(4-methyl-imidazol-1-yl)-phenyl]-amine and 2-hydroxy benzotrifluoride in analogy to example 3. Chromatography on silica gel using ethyl acetate as an eluent gave the title compound as a colorless solid in 99% yield.

MS ISP (m/e): 501.3 (100) [(M+H)⁺]

¹H NMR (CDCl₃, 300 MHz): δ (ppm)=7.60 (s, 1H), 7.55-7.30 (m, 4H), 7.15-6.85 (m, 3H), 6.85 (s, 1H), 5.20 (m, 1H), 3.52 (s, 3H), 2.29 (s, 3H), 1.36 (d; 6H).

EXAMPLE 17

N-(4-Chloro-phenyl)-6-isopropoxy-N'-[3-methoxy-4-(4-methyl-imidazol-1-yl)-phenyl]-N-methyl-[1,3,5]triazine-2,4-diamine

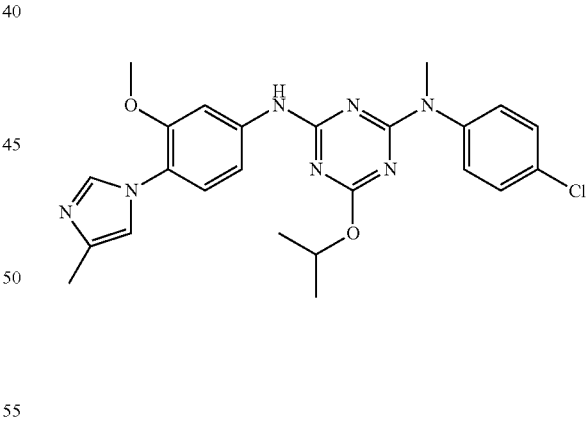

This compound was prepared from (4-chloro-6-isopropoxy-[1,3,5]triazin-2-yl)-[₃-methoxy-4-(4-methyl-imidazol-1-yl)-phenyl]-amine and 4-chloro-N-methyl aniline in analogy to example 1c. Chromatography on Si—NH2 gel (Isolute) using ethyl acetate as an eluent gave the title compound as a colorless solid in 27% yield.

MS ISP (m/e): 480.3 (100) [(M+H)⁺]

¹H NMR (CDCl₃, 300 MHz): δ (ppm)=7.60 (s, 1H), 7.40-7.35 (m, 4H), 7.27 (d, 2H), 7.15-6.90 (m, 3H), 6.85 (s, 1H), 5.21 (s broad, 1H), 4.40-3-30 (s very broad, 3H), 3.51 (s, 3H), 2.30 (s, 3H), 1.36 (s broad, 6H).

EXAMPLE 18

[3-Methoxy-4-(4-methyl-imidazol-1-yl)-phenyl]-(4-methoxy-6-methyl-[1,3,5]triazin-2-yl)-amine

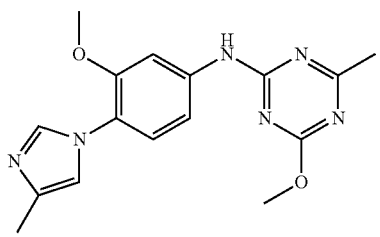 [SMILES: COc1nc(C)nc(Nc2ccc(-n3cnc(C)c3)c(OC)c2)n1]

a) 2-Chloro-4-methoxy-6-methyl-[1,3,5]triazine

A solution of 2,4-dichloro-6-methoxy-1,3,5-Triazine (1.0 g, 5.56 mmol) in 10 ml of dioxane was treated with a 1.2 molar solution of dimethylzinc in toluene (4.63 ml, 5.56 mmol). The mixture was stirred overnight at room temperature, poured into 100 ml of water and extracted with ethyl acetate. Chromatography on silica gel using heptane/ethyl acetate 9:1 v/v gave the title compound (225 mg, 25%) as a colorless solid.
MS (m/e): 159.0 (32) [(M$^+$)]
$^1$H NMR (DMSO-D$_6$, 300 MHz): δ (ppm)=4.00 (s, 3H), 2.51 (s, 3H).

b) [3-Methoxy-4-(4-methyl-imidazol-1-yl)-phenyl]-(4-methoxy-6-methyl-[1,3,5]triazin-2-yl)-amine This compound was prepared from 3-methoxy-4-(4-methyl-imidazol-1-yl)-phenylamine and 2-chloro-4-methoxy-6-methyl-[1,3,5]triazine in analogy to example 1c. It was purified by chromatography on Si—NH2 (Isolute) using ethyl acetate as an eluent to give the title compound as a slightly yellowish solid in 32% yield.
MS ISP (m/e): 480.3 (100) [(M+H)$^+$]
$^1$H NMR (CDCl$_3$, 300 MHz): δ (ppm)=7.69 (s, 1H), 7.65 (s, 1H), 7.21 (d, 1H), 7.08 (dxd, 1H), 6.88 (s, 1H), 4.03 (s, 3H), 3.87 (s, 3H), 2.48 (s, 3H), 2.29 (s, 3H).

EXAMPLE 19

(4,6-Diisopropoxy-[1,3,5]triazin-2-yl)-[3-methoxy-4-(4-methyl-imidazol-1-yl)-phenyl]-amine

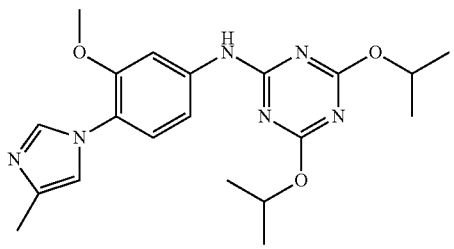 [SMILES: COc1cc(Nc2nc(OC(C)C)nc(OC(C)C)n2)ccc1-n1cnc(C)c1]

To 2-propanol (321 mg, 5.34 mmol) was added metallic sodium (9 mg, 0.39 mmol). The resulting alcoholate-solution was treated with (4-chloro-6-isopropoxy-[1,3,5]triazin-2-yl)-[3-methoxy-4-(4-methyl-imidazol-1-yl)-phenyl]-amine (100 mg, 0.27 mmol) and the resulting mixture refluxed for 3 hours. Water was added and the product extracted with ethyl acetate. The crude material was purified by chromatography on Si—NH2 gel (Isolute) using ethyl acetate as an eluent to give the title compound as a colorless solid (71 mg, 67%).
MS ISP (m/e): 399.2 (100) [(M+H)$^+$]
$^1$H NMR (CDCl$_3$, 300 MHz): δ (ppm)=7.63 (d, 1H), 7.49 (d, 1H), 7.22 (d, 1H), 7.25-7.15 (m, 2H), 7.08 (dxd, 1H), 6.87 (s, 1H), 5.32 (sept., 2H), 3.86 (s, 3H), 2.30 (s, 3H); 1.40 (d, 12H).

EXAMPLE 20

6-Methoxy-N-(2-methoxy-ethyl)-N'-[3-methoxy-4-(4-methyl-imidazol-1-yl)-phenyl]-N-methyl-[1,3,5]triazine-2,4-diamine

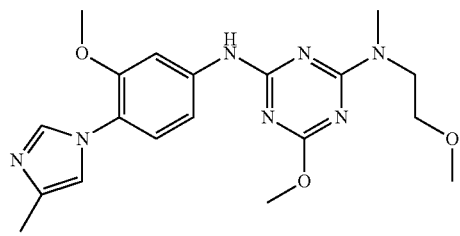 [SMILES: COCCN(C)c1nc(Nc2ccc(-n3cnc(C)c3)c(OC)c2)nc(OC)n1]

This compound was prepared from (4-chloro-6-methoxy-[1,3,5]triazin-2-yl)-[3-methoxy-4-(4-methyl-imidazol-1-yl)-phenyl]-amine and N-(2-methoxyethyl)methylamine in analogy to example 1c. It was purified by chromatography on Si—NH2 (Isolute) using ethyl acetate as an eluent to give the title compound as a slightly yellowish solid in 51% yield.
MS ISP (m/e): 400.2 (100) [(M+H)$^+$]
$^1$H NMR (CDCl$_3$, 300 MHz): δ (ppm)=7.78 & 7.65 (two s, total 1H), 7.63 (d, 1H), 7.16 (d, 1H), 7.05-6.95 (m, 2H), 6.87 (s, 1H), 3.96 & 3.94 (two s, total 3H), 3.85 (s, 3H), 3.90-3.75 (m, 2H), 3.15-3.05 (m, 2H), 3.36 & 3.35 (two s, total 3H), 3.26 & 3.23 (two s, total 3H), 2.29 (s, 3H).

EXAMPLE 21

(1-{4-Methoxy-6-[3-methoxy-4-(4-methyl-imidazol-1-yl)-phenylamino]-[1,3,5]triazin-2-yl}-piperidin-4-yl)-acetic acid ethyl ester

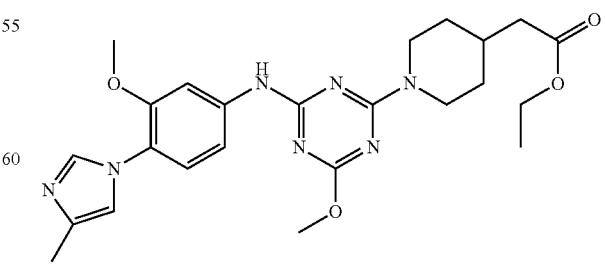

A suspension of (4-chloro-6-methoxy-[1,3,5]triazin-2-yl)-[3-methoxy-4-(4-methyl-imidazol-1-yl)-phenyl]-amine (100 mg, 0.29 mmol) and ethyl-2-(piperidin-4-yl)acetate hydrochloride (63 mg, 0.30 mmol) in 3 ml of methanol was treated with triethylamine (0.13 ml, 0.92 mmol). The mixture was stirred for 3 hours at room temperature, concentrated and the product purified by chromatography on silica gel using ethyl acetate as an eluent. The title compound was isolated as a colorless solid (137 mg, 99%).

MS ISP (m/e): 482.3 (100) [(M+H)$^+$]

$^1$H NMR (CDCl$_3$, 300 MHz): δ (ppm)=7.68 (d, 1H), 7.62 (s, 1H), 7.16 (d, 1H), 7.00-6.90 (m, 2H), 6.87 (s, 1H), 4.79 (d broad, 2H), 4.15 (qa, 2H), 3.94 (s, 3H), 3.84 (s, 3H), 2.92 (t broad, 2H), 2.35-2.20 (m, 5H), 2.20-2.00 (m, 1H), 1.81 (d broad, 2H), 1.35-1.15 (m, 5H).

EXAMPLE 22

N-[3-Methoxy-4-(4-methyl-imidazol-1-yl)-phenyl]-N',N'-dimethyl-6-(4-methyl-piperazin-1-yl)-[1,3,5]triazine-2,4-diamine

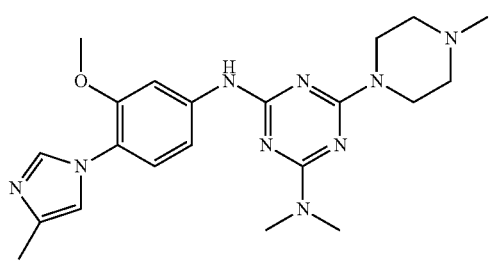 [SMILES: COc1cc(Nc2nc(N(C)C)nc(N3CCN(C)CC3)n2)ccc1-n1cnc(C)c1]

6-Chloro-N-[3-methoxy-4-(4-methyl-imidazol-1-yl)-phenyl]-N',N'-dimethyl-[1,3,5]triazine-2,4-diamine (100 mg, 0.28 mmol) was treated with N-methylpiperidine (0.31 ml, 2.78 mmol). The mixture was heated to 50° C. for 30 minutes, diluted with water and extracted with ethyl acetate. Purification by chromatography on silica gel using ethyl acetate as an eluent to gave the title compound (114 mg, 97%) as a yellowish gum.

MS ISP (m/e): 424.3 (100) [(M+H)$^+$]

$^1$H NMR (CDCl$_3$, 300 MHz): δ (ppm)=7.79 (d, 1H), 7.61 (d, 1H), 7.13 (d, 1H), 6.93 (dxd, 1H), 6.86 (s, 1H), 6.79 (s, 1H), 3.90-3.80 (m, 7H), 3.15 (s, 6H), 2.43 (t broad, 4H), 2.35 (s, 3H), 2.29 (s, 3H).

EXAMPLE 23

[4,6-Bis-(2-trifluoromethyl-phenoxy)-[1,3,5]triazin-2-yl]-[3-methoxy-4-(4-methyl-imidazol-1-yl)-phenyl]-amine

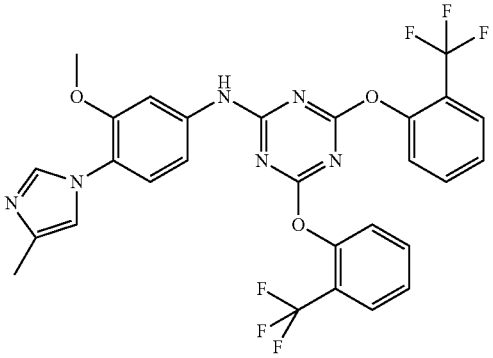 [SMILES: COc1cc(Nc2nc(Oc3ccccc3C(F)(F)F)nc(Oc3ccccc3C(F)(F)F)n2)ccc1-n1cnc(C)c1]

a) (4,6-Dichloro-[1,3,5]triazin-2-yl)-[3-methoxy-4-(4-methyl-imidazol-1-yl)-phenyl]-amine A solution of 3-methoxy-4-(4-methyl-imidazol-1-yl)-phenylamine (1.0 g, 4.92 mmol) and triethylamine (0.75 ml, 5.42 mmol) in 15 ml of methanol was cooled in an ice-bath and cyanuric chloride (889 mg, 4.82 mmol) added portionwise. The mixture was stirred for 1 hour at 0° C. Filtration of the precipitate gave the title compound (1.115 g, 65%) as a slightly brownish solid.

MS ISP (m/e): 351.2 (100) & 353.1 (56) [(M+H)$^+$]

$^1$H NMR (DMSO-D$_6$, 300 MHz): δ (ppm)=11.29 (s, 1H), 7.81 (s, 1H), 7.54 (d, 1H), 7.41 (d, 1H), 7.29 (dxd, 1H), 7.13 (s, 1H), 3.81 (s, 3H), 2.16 (s, 3H).

b) [4,6-Bis-(2-trifluoromethyl-phenoxy)-[1,3,5]triazin-2-yl]-[3-methoxy-4-(4-methyl-imidazol-1-yl)-phenyl]-amine A mixture of 2-hydroxybenzotrifluoride (95 mg, 0.59 mmol) and potassium carbonate (87 mg, 0.63 mmol) in 10 ml of acetonitrile was treated with (4,6-dichloro-[1,3,5]triazin-2-yl)-[3-methoxy-4-(4-methyl-imidazol-1-yl)-phenyl]-amine. The suspension was refluxed overnight, diluted with water and extracted with ethyl acetate. Chromatography on silica gel using ethyl acetate as the eluent gave the title compound (17 mg, 10%) as a slightly brownish solid.

MS ISP (m/e): 603.2 (100) [(M+H)$^+$]

¹H NMR (CDCl₃, 300 MHz): δ (ppm)=7.69 (d, 2H), 7.65-7.50 (m, 3H), 7.45-7.20 (m, 5H), 7.04 (d, 1H), 6.84 (d, 2H), 3.56 & 3.49 (two s, total 3H), 2.28 (s, 3H).

EXAMPLE 24

3-({4-Methoxy-6-[3-methoxy-4-(4-methyl-imidazol-1-yl)-phenylamino]-[1,3,5]triazin-2-yl}-methyl-amino)-propane-1,2-diol

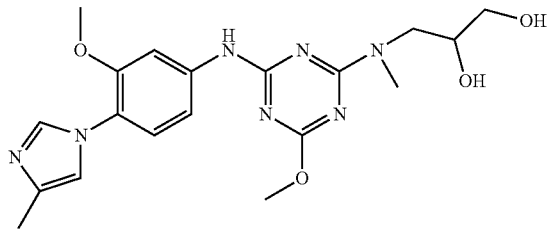 [SMILES: COc1nc(Nc2ccc(-n3cnc(C)c3)c(OC)c2)nc(N(C)CC(O)CO)n1]

A mixture of (4-chloro-6-methoxy-[1,3,5]triazin-2-yl)-[₃-methoxy-4-(4-methyl-imidazol-1-yl)-phenyl]-amine (100 mg, 0.29 mmol) and 3-methyl-1,2-propanediol (606 mg, 5.76 mmol) was heated for 2 hours at 60° C. The reaction mixture was diluted with water and extracted with ethyl acetate. The organic phase was dried, concentrated and the title compound (85 mg, 71%) isolated as a slightly brownish solid by trituration in diethyl ether.

MS ISP (m/e): 416.3 (100) [(M+H)⁺]

¹H NMR (CDCl₃, 300 MHz): δ (ppm)=7.75-7.60 (m, 1H), 7.20-7.00 (m, 3H), 6.87 (s broad, 1H), 4.05-3.90 (m, 3H), 3.84 (s, 3H), 3.90-3.40 (m, 7H), 3.26 & 3.24 (two s, total 3H), 2.29 (s, 3H).

EXAMPLE 25

[4-(4-Chloro-benzyloxy)-6-methoxy-[1,3,5]triazin-2-yl]-[3-methoxy-4-(4-methyl-imidazol-1-yl)-phenyl]-amine

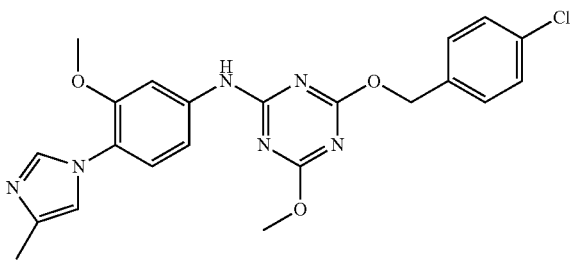 [SMILES: COc1nc(Nc2ccc(-n3cnc(C)c3)c(OC)c2)nc(OCc2ccc(Cl)cc2)n1]

To a solution of 4-chlorobenzyl alcohol (45 mg, 0.32 mmol) in 10 ml of tetrahydrofuran was added metallic sodium (7 mg, 0.30 mmol). The mixture was stirred until the sodium dissolved. (4-Chloro-6-methoxy-[1,3,5]triazin-2-yl)-[3-methoxy-4-(4-methyl-imidazol-1-yl)-phenyl]-amine (100 mg, 0.29 mmol) was added and the mixture refluxed for 4 hours, diluted with water and extracted with ethyl acetate. The product was purified by chromatography on Si—NH2 (Isolute) using ethyl acetate as a solvent to give the title compound (26 mg, 20%) as a colorless solid.

MS ISP (m/e): 453.2 (100) [(M+H)⁺]

¹H NMR (CDCl₃, 300 MHz): δ (ppm)=7.64 (s, 1H), 7.50 (s broad, 1H), 7.45-7.25 (m, 5H), 7.20 (d, 1H), 7.10 (d, 1H), 6.88 (s, 1H), 5.41 (s, 2H), 4.03 (s, 3H), 3.85 (s, 3H), 2.30 (s, 3H).

EXAMPLE 26

(1-{4-Methoxy-6-[3-methoxy-4-(4-methyl-imidazol-1-yl)-phenylamino]-[1,3,5]triazin-2-yl}-piperidin-4-yl)-acetic acid

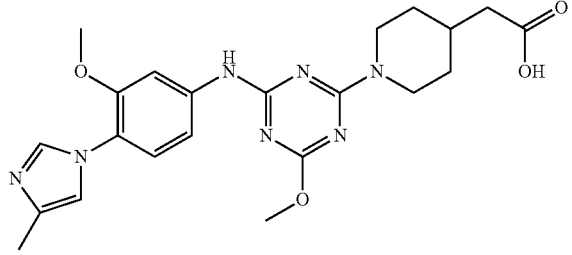 [SMILES: COc1nc(Nc2ccc(-n3cnc(C)c3)c(OC)c2)nc(N2CCC(CC(=O)O)CC2)n1]

4-Piperidineacetic acid hydrochloride (381 mg, 2.12 mmol) was suspended in 10 ml of methanol. Triethylamine (0.9 ml, 6.45 mmol) was added, followed by (4-chloro-6-methoxy-[1,3,5]triazin-2-yl)-[₃-methoxy-4-(4-methyl-imidazol-1-yl)-phenyl]-amine (700 mg, 2.02 mmol). The resulting mixture was stirred overnight at room temperature, concentrated and subjected to column chromatography on Si—NH2 (Isolute) using dichloromethane/methanol 95:5 v/v as an eluent. The material isolated was further purified by several triturations in water to give the final compound (792 mg, 87%) as a slightly brownish solid.

MS ISN (m/e): 452.2 (100) [(M−H)⁻].

¹H NMR (DMSO-D₆, 300 MHz): δ (ppm)=12.20 (s broad, 1H), 9.72 (s, 1H), 7.89 (s, 1H), 7.67 (d, 1H), 7.30-7.15 (m, 2H), 7.04 (s, 1H), 4.65 (s broad, 2H), 3.86 (s, 3H), 3.79 (s, 3H), 3.10-2.80 (m, 2H), 2.19 (d, 2H), 2.14 (s, 3H), 2.05-1.90 (m, 1H), 1.74 (d broad, 2H), 1.25-1.05 (m, 2H).

EXAMPLE 27

(1-[4-[4-(2-Chloro-pyridin-3-yloxy)-6-methoxy-[1,3,5]triazin-2-ylamino]-2-methoxy-phenyl]-1H-imidazol-4-yl)-methanol

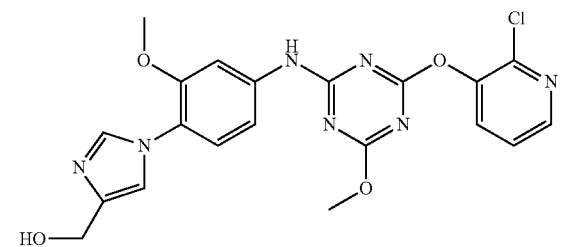 [SMILES: COc1nc(Nc2ccc(-n3cnc(CO)c3)c(OC)c2)nc(Oc2cccnc2Cl)n1]

a) [1-(2-Methoxy-4-nitro-phenyl)-1H-imidazol-4-yl]-methanol

A mixture of 1-fluoro-2-methoxy-4-nitro-benzene (1.0 g, 5.8 mmol), (1H-imidazol-4-yl)-methanol (602 mg, 6.1 mmol) and cesium carbonate (2.86 g, 8.8 mmol) in 40 ml of acetonitrile was refluxed overnight. The reaction mixture was concentrated in vacuo, diluted with water and extracted with ethyl acetate. Chromatography on Si—NH2 (Isolute) using ethyl acetate as an eluent gave the title compound as a yellowish solid.

MS ISP (m/e): 250.1 (51) [(M+H)$^+$]

$^1$H NMR (CDCl$_3$, 300 MHz): δ (ppm)=8.00-7.85 (m, 3H), 7.45 (d, 1H), 7.26 (d, 1H), 4.70 (s, 2H), 4.01 (s, 3H).

b) [1-(4-Amino-2-methoxy-phenyl)-1H-imidazol-4-yl]methanol

[1-(2-Methoxy-4-nitro-phenyl)-1H-imidazol-4-yl]methanol (500 mg, 2.0 mmol) and stannous chloride dehydrate (2.35 g, 10.4 mmol) were suspended in a mixture of 40 ml of ethyl acetate and 20 ml of methanol. The reaction mixture was refluxed for 1 hour, cooled to room temperature and diluted with aqueous sodium hydrogencarbonate solution. Extraction with ethyl acetate gives the title compound (311 mg, 71%) as a yellowish viscous oil.

MS ISP (m/e): 220.1 (46) [(M+H)$^+$]

$^1$H NMR (CDCl$_3$, 300 MHz): δ (ppm)=7.61 (s, 1H), 7.01 (d, 2H), 6.35-6.25 (m, 2H), 4.66 (s, 2H), 3.85 (s broad, 2H), 3.77 (s, 3H).

c) {1-[4-(4-Chloro-6-methoxy-[1,3,5]triazin-2-ylamino)-2-methoxy-phenyl]-1H-imidazol-4-yl}-methanol This compound was prepared in analogy to example 8 from [1-(4-amino-2-methoxy-phenyl)-1H-imidazol-4-yl]-methanol, triethylamine and 2,4-dichloro-6-methoxy-1,3,5-triazine. The title compound was isolated as a brownish solid in 61% yield.

MS ISN (m/e): 361.3 (100) & 363.4 (34) [(M−H)$^−$].

$^1$H NMR (DMSO-D$_6$, 300 MHz): δ (ppm)=10.86 (s broad, 1H), 7.79 (d, 1H), 7.45-7.25 (m, 2H), 7.22 (s, 1H), 4.93 (t broad, 1H), 4.39 (d broad, 2H), 4.00 (s, 3H), 3.82 (s, 3H).

d) (1-{4-[4-(2-Chloro-pyridin-3-yloxy)-6-methoxy-[1,3,5]triazin-2-ylamino]-2-methoxy-phenyl}-1H-imidazol-4-yl)-methanol This compound was prepared in analogy to example 3 from {1-[4-(4-chloro-6-methoxy-[1,3,5]triazin-2-ylamino)-2-methoxy-phenyl]-1H-imidazol-4-yl}-methanol and 2-chloro-3-hydroxypyridine. The title compound was isolated as a slightly brownish solid in 43% yield.

MS ISP (m/e): 220.1 (46) [(M+H)$^+$]

$^1$H NMR (DMSO-D$_6$, 300 MHz): δ (ppm)=10.50 (s broad, 1H), 8.39 (dxd, 1H), 8.00 (d, 1H), 7.90-7.65 (m, 2H), 7.65-7.50 (m, 1H), 7.40-7.10 (m, 2H), 4.39 (s, 2H), 3.96 (s, 3H), 3.80 (s broad, 3H).

EXAMPLE 28

[4-(2-Chloro-pyridin-3-yloxy)-6-methoxy-[1,3,5]triazin-2-yl]-(4-imidazol-1-yl-phenyl)-amine

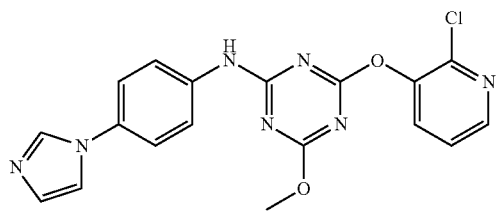 [SMILES: COc1nc(Nc2ccc(-n3ccnc3)cc2)nc(Oc2cccnc2Cl)n1]

a) (4-Chloro-6-methoxy-[1,3,5]triazin-2-yl)-(4-imidazol-1-yl-phenyl)-amine

This compound was prepared in analogy to example 8 from 4-(imidazol-1-yl)-aniline, triethylamine and 2,4-dichloro-6-methoxy-1,3,5-triazine. The title compound was isolated as a slightly brownish solid in 84% yield.

MS ISP (m/e): 303.3 (100) & 305.2 (47) [(M+H)$^+$]

$^1$H NMR (DMSO-D$_6$, 300 MHz): δ (ppm)=10.82 & 10.70 (two broad s, total 1H), 8.22 (s, 1H), 7.90-7.60 (m, 5H), 7.11 (s, 1H), 3.97 (s, 3H).

b) [4-(2-Chloro-pyridin-3-yloxy)-6-methoxy-[1,3,5]-triazin-2-yl]-(4-imidazol-1-yl-phenyl)-amine This compound was prepared in analogy to example 3 from (4-chloro-6-methoxy-[1,3,5]triazin-2-yl)-(4-imidazol-1-yl-phenyl)-amine and 2-chloro-3-hydroxypyridine. The title compound was isolated as a colorless solid in 37% yield.

MS ISP (m/e): 396.1 (100) & 398.2 (44) [(M+H)$^+$]

$^1$H NMR (CDCl$_3$, 300 MHz): δ (ppm)=8.37 (d, 1H), 7.81 (s, 1H), 7.60 (dxd, 1H), 7.45-7.30 (m, 4H), 7.30-7.20 (m, 3H), 4.00 (s, 3H).

EXAMPLE 29

(S)-2-({4-Methoxy-6-[3-methoxy-4-(4-methyl-imidazol-1-yl)-phenylamino]-[1,3,5]triazin-2-yl}-methyl-amino)-2-phenyl-ethanol

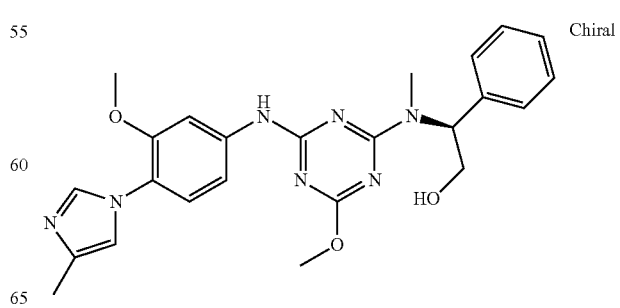

a) (R)-2-Methylamino-2-phenyl-ethanol

Lithium aluminum hydride (1.84 g, 43 mmol) was suspended in 30 ml of tetrahydrofuran and cooled in an ice-bath. A solution of (R)-methylamino-phenyl acetic acid (1.0 g, 6 mmol) in 10 ml of tetrahydrofuran was slowly added over a period of 20 minutes. The resulting mixture was stirred for 1 hour at 0°, 4 hours at room temperature and then refluxed overnight. The mixture was cooled and carefully hydrolysed by addition of 50 ml 15% aqueous sodium hydroxide. Extraction with ethyl acetate gives a crude oil which was purified by chromatography on silica gel using heptane/ethyl acetate 9:1 v/v to give the title compound as a slightly yellowish oil (0.36 g, yield=39%).

MS ISP (m/e): 152.2 (100) [(M+H)$^+$]

$^1$H NMR (CDCl$_3$, 300 MHz): δ (ppm)=7.40-7.25 (m, 5H), 3.75-3.35 (m, 3H), 2.36 (s, 3H), 1.80 (s broad, 2H).

b) (S)-2-({4-Methoxy-6-[3-methoxy-4-(4-methyl-imidazol-1-yl)-phenylamino]-[1,3,5]triazin-2-yl}-methyl-amino)-2-phenyl-ethanol This compound was prepared from (4-chloro-6-methoxy-[1,3,5]triazin-2-yl)-[3-methoxy-4-(4-methyl-imidazol-1-yl)-phenyl]-amine and (R)-2-methylamino-2-phenyl-ethanol in analogy to example 1c. Purification by chromatography on Si—NH2 gel (Isolute) using ethyl acetate as an eluent gave the title compound as a colorless solid in 32% yield.

MS ISP (m/e): 462.2 (100) [(M+H)$^+$]

$^1$H NMR (CDCl$_3$, 300 MHz): δ (ppm)=7.80-6.80 (m, 10H), 6.23 (d broad, 1H), 4.35-4.05 (m, 2H), 3.97 (d, 3H), 3.85-3.65 (m, 3H), 2.99 (d, 3H), 2.28 (s, 3H), 1.61 (s broad, >1H).

EXAMPLE 30

2-{4-Methoxy-6-[3-methoxy-4-(4-methyl-imidazol-1-yl)-phenylamino]-[1,3,5]triazin-2-yl}-propan-2-ol

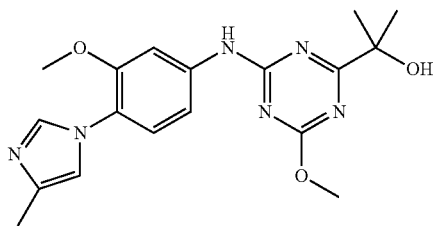 [SMILES: COc1nc(Nc2ccc(-n3cnc(C)c3)c(OC)c2)nc(C(C)(C)O)n1]

a) 4-Methoxy-6-[3-methoxy-4-(4-methyl-imidazol-1-yl)-phenylamino]-[1,3,5]triazine-2-carboxylic acid methyl ester A solution of (4-chloro-6-methoxy-[1,3,5]triazin-2-yl)-[3-methoxy-4-(4-methyl-imidazol-1-yl)-phenyl]-amine (0.35 g, 1.0 mmol) in a mixture of 7 ml methanol and 3.5 ml ethyl acetate was treated with triethylamine (0.21 ml, 1.5 mmol) and tris(dibenzylideneacetone) dipalladium dichloromethane-complex (70 mg, 0.09 mmol). The mixture was transferred to an autoclave, flushed with carbon monoxide and hold 20 hours at 80° C. under a pressure of 5 bar of carbon monoxide. After cooling and evacuating the carbon monoxide, the mixture was concentrated to about 2 ml and diluted again with a mixture of ethyl acetate/methanol 9:1 v/v. The title compound precipitated as an intensely yellow solid after cooling in the refrigerator for 17 hours. Yield=55%.

MS ISP (m/e): 371.3 (100) [(M+H)$^+$]

$^1$H NMR (CDCl$_3$, 300 MHz): δ (ppm)=7.80-7.50 (m, 2H), 7.22 (s, 1H), 7.08 (s broad, 1H), 6.89 (s, 1H), 4.12 (s, 3H), 4.03 (s, 3H), 3.88 (s, 3H), 2.30 (s, 3H).

b) 2-[4-Methoxy-6-[3-methoxy-4-(4-methyl-imidazol-1-yl)-phenylamino]-[1,3,5]triazin-2-yl]-propan-2-ol A slurry of 4-methoxy-6-[3-methoxy-4-(4-methyl-imidazol-1-yl)-phenylamino]-[1,3,5]triazine-2-carboxylic acid methyl ester (105 mg, 0.28 mmol) in 2 ml of tetrahydrofuran was treated at room temperature with a 3M solution of methyl magnesium chloride (0.5 ml, 1.5 mmol) in tetrahydrofuran. After stirring for 90 minutes at room temperature, the heterogenous mixture was hydrolyzed by addition of 20 ml of water. The mixture was extracted with ethyl acetate and the final product purified by chromatography on Si—NH2 gel (Isolute) using cyclohexane/ethyl acetate (gradient 60 to 100% ethyl acetate). The title compound was isolated as a colorless solid in a yield of 43%.

MS ISP (m/e): 371.2 (100) [(M+H)$^+$]

$^1$H NMR (CDCl$_3$, 300 MHz): δ (ppm)=7.67 (s, 1H), 7.40 (s broad, 1H), 7.22 (s, 1H), 7.10 (s broad, 1H), 6.90 (s, 1H), 4.22 (s broad, 1H), 4.07 (s, 3H), 3.88 (s, 3H), 2.31 (s, 3H), 1.56 (s, 6H).

EXAMPLE 31

N-[3-Methoxy-4-(4-methyl-imidazol-1-yl)-phenyl]-N',N'-dimethyl-6-(2-trifluoromethyl-phenoxy)-[1,3,5]triazine-2,4-diamine

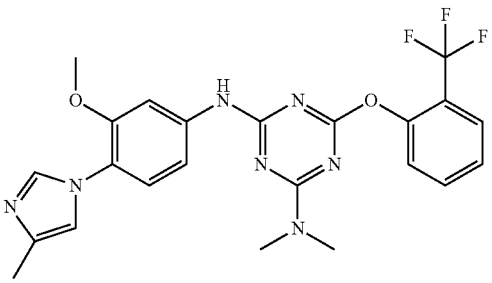 [SMILES: COc1cc(Nc2nc(Oc3ccccc3C(F)(F)F)nc(N(C)C)n2)ccc1-n1cnc(C)c1]

6-Chloro-N-[3-methoxy-4-(4-methyl-imidazol-1-yl)-phenyl]-N',N'-dimethyl-[1,3,5]triazine-2,4-diamine (200 mg, 0.56 mmol) in 7 ml acetonitrile was treated with 2-hydroxybenzotrifluoride (95 mg, 0.59 mmol) and potassium carbonate (85 mg, 0.62 mmol). The resulting mixture was stirred under reflux for 5 days. The mixture was then diluted with 25 ml of water and extracted with ethyl acetate. Chromatography on silica gel using ethyl acetate as a solvent and subsequent crystallization from methanol gave the title compound as colorless solid (42 mg, 16%).

MS ISP (m/e): 486.3 (100) [(M+H)$^+$]

$^1$H NMR (CDCl$_3$, 300 MHz): δ (ppm)=7.69 (d, 1H), 7.65-7.55 (m, 3H), 7.40-7.30 (m, 2H), 7.10 (d, 1H), 7.00 (s, 1H), 6.93 (d broad, 1H), 6.85 (s, 1H), 3.73 (s broad, 2H), 3.21 (s, 3H), 3.09 (s, 3H), 2.29 (s, 3H).

EXAMPLE 32

[4-(4-Fluoro-phenyl)-6-methoxy-[1,3,5]triazin-2-yl]-[3-methoxy-4-(4-methyl-imidazol-1-yl)-phenyl]-amine

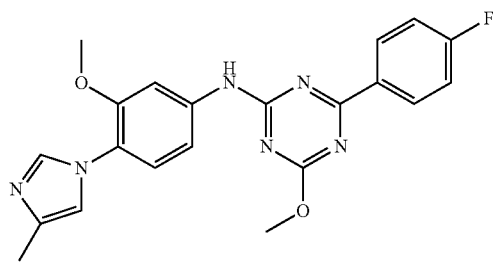 [SMILES: COc1nc(Nc2ccc(-n3cnc(C)c3)c(OC)c2)nc(-c2ccc(F)cc2)n1]

A mixture of (4-chloro-6-methoxy-[1,3,5]triazin-2-yl)-[3-methoxy-4-(4-methyl-imidazol-1-yl)-phenyl]-amine (150 mg, 0.43 mmol), 4-fluorobenzeneboronic acid (67 mg, 0.48 mmol), tetrakis-(triphenylphosphin)-palladium (20 mg, 0.02 mmol) and sodium carbonate (92 mg, 0.87 mmol) in 3 ml of dioxane was refluxed overnight. The mixture was diluted with water, extracted with ethyl acetate and purified by chromatography on silica gel using ethyl acetate as an eluent to give the title compound as a colorless solid (84 mg, yield=47%).

MS ISP (m/e): 486.3 (100) [(M+H)$^+$]

$^1$H NMR (CDCl$_3$, 300 MHz): δ (ppm)=8.49 (t broad, 2H), 7.69 (d, 2H), 7.40 (s broad, 1H), 7.25-7.10 (m, 4H), 6.91 (s, 1H), 4.12 (s, 3H), 3.91 (s, 3H), 2.32 (s, 3H).

EXAMPLE 33

[4-Chloro-6-(4-chloro-benzyl)-[1,3,5]triazin-2-yl]-[3-methoxy-4-(4-methyl-imidazol-1-yl)-phenyl]-amine

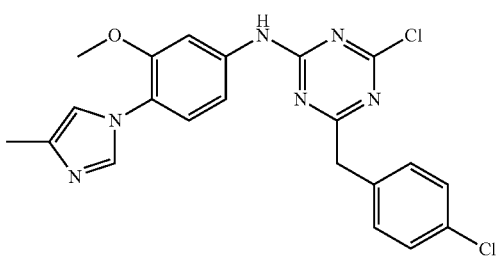 [SMILES: COc1cc(Nc2nc(Cl)nc(Cc3ccc(Cl)cc3)n2)ccc1-n1cnc(C)c1]

a) 2,4-Dichloro-6-(4-chloro-benzyl)-[1,3,5]triazine

An aliquot (12 mL) of a solution of 4-chlorobenzyl chloride (3.94 g, 24.0 mmol) in diethyl ether (60 mL) was added to a mixture of magnesium turnings (0.58 g, 24 mmol) and diethyl ether (20 mL). The mixture was heated to reflux, and subsequently, the residual solution was added drop wise over 1 h at 20 to 30° C. Stirring was continued at 20° C. for 2 hours, and thereafter, the freshly prepared Grignard solution was added drop wise over 15 min at 10 to 15° C. to a solution of cyanuric chloride (3.76 g, 20 mmol) in toluene (40 mL) cooled in an ice-bath.

The reaction mixture was stirred at 0° C. for 1 h and thereafter allowed to warm to 20° C. over 2 h. Stirring was continued for 15 h at 20° C. The reaction mixture was poured onto saturated aqueous ammonium chloride solution and the mixture was extracted with ethyl acetate. The organic layer was washed with water, dried over sodium sulfate, and the solvent was removed under reduced pressure. The residue was stirred with heptane (20 mL) for 30 minutes at 20° C. The solid formed was isolated by filtration to give the title compound (2.4 g, 44%) as a light yellow solid. $^1$H-NMR (CDCl$_3$, 300 MHz): δ (ppm)=7.31 (s, 4H), 4.14 (s, 2H).

b) [4-Chloro-6-(4-chloro-benzyl)-[1,3,5]triazin-2-yl]-[3-methoxy-4-(4-methyl-imidazol-1-yl)-phenyl]-amine 2,4-Dichloro-6-(4-chloro-benzyl)-[1,3,5]triazine (0.78 g, 2.8 mmol) was added at 5° C. to a solution of 3-methoxy-4-(4-methyl-imidazol-1-yl)-phenylamine (0.61 g, 3.0 mmol) and triethylamine (0.36 ml, 0.26 mmol) in 15 ml of methanol. The mixture was stirred at 5° C. for 1 h and thereafter evaporated under reduced pressure. The residual material was purified by chromatography on silica gel using heptane/0-100% ethyl acetate as eluent to give the title compound (0.53 g, 40%) as a yellow viscous oil.

MS ISP (m/e): 441.2 [(M+H)$^+$].

$^1$H NMR (CDCl$_3$, 300 MHz): δ (ppm)=7.67 (s, 1H), 7.60 (s, 1H), 7.30 (m, 4H), 7.20 (d, 1H), 7.02 (dd, 1H), 6.89 (s, 1H), 4.03 (s broad, 2H), 3.85 (s broad, 3H), 3.72 (s broad, 3H), 2.30 (s, 3H).

EXAMPLE 34

4-(4-Chloro-benzyl)-6-[3-methoxy-4-(4-methyl-imidazol-1-yl)-phenylamino]-[1,3,5]triazine-2-carboxylic acid methyl ester

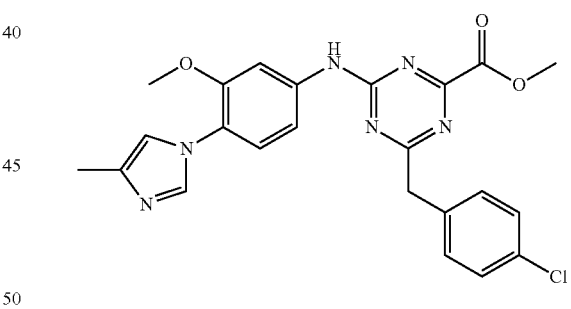

This compound was prepared from [4-chloro-6-(4-chloro-benzyl)-[1,3,5]triazin-2-yl]-[3-methoxy-4-(4-methyl-imidazol-1-yl)-phenyl]-amine (0.60 g, 1.36 mmol) in analogy to example 30 a. The crude product was purified by chromatography on silica gel using heptane/0-80% ethyl acetate as eluent to give the title compound (0.41 g, 64%) as a yellow solid.

MS ISP (m/e): 465.3 [(M+H)$^+$].

$^1$H NMR (CDCl$_3$, 300 MHz): δ (ppm)=7.66 (s, 1H), 7.58 (s, 1H), 7.30 (m, 4H), 7.20 (d, 1H), 6.98 and 7.05 (2 dd, 1H), 6.88 (s, 1H), 4.19 and 4.02 (2 s broad, 2H), 4.01 and 3.97 (2 s broad, 3H), 3.80 and 3.70 (2 s broad, 3H), 2.30 (s, 3H).

The invention claimed is:
1. A compound selected from the group consisting of [3-methoxy-4-(4-methyl-imidazol-1-yl)-phenyl]-(4-methoxy-6-piperidin-1-yl-[1,3,5]triazin-2-yl)-amine;

(1-{4-methoxy-6-[3-methoxy-4-(4-methyl-imidazol-1-yl)-phenylamino]-[1,3,5]triazin-2-yl}-piperidin-4-yl)-acetic acid ethyl ester; and (1-{4-methoxy-6-[3-methoxy-4-(4-methyl-imidazol-1-yl)-phenylamino]-[1,3,5]triazin-2-yl}-piperidin-4-yl)-acetic acid or a pharmaceutically active acid addition salt thereof.

2. A compound selected from the group consisting of

[3-methoxy-4-(4-methyl-imidazol-1-yl)-phenyl]-[4-methoxy-6-(2-trifluoromethyl-phenoxy)-[1,3,5]triazin-2-yl]-amine;

[4-(4-fluoro-phenoxy)-6-methoxy-[1,3,5]triazin-2-yl]-[3-methoxy-4-(4-methyl-imidazol-1-yl)-phenyl]-amine;

[3-methoxy-4-(4-methyl-imidazol-1-yl)-phenyl]-[4-methoxy-6-(3,4,5-trifluoro-phenoxy)-[1,3,5]triazin-2-yl]-amine;

[4-(2,4-dichloro-phenoxy)-6-methoxy-[1,3,5]triazin-2-yl]-[3-methoxy-4-(4-methyl-imidazol-1-yl)-phenyl]-amine;

[4-(2-chloro-pyridin-3-yloxy)-6-methoxy-[1,3,5]triazin-2-yl]-[3-methoxy-4-(4-methyl-imidazol-1-yl)-phenyl]-amine;

[4-isopropoxy-6-(2-trifluoromethyl-phenoxy)-[1,3,5]triazin-2-yl]-[3-methoxy-4-(4-methyl-imidazol-1-yl)-phenyl]-amine;

(4,6-diisopropoxy-[1,3,5]triazin-2-yl)-[3-methoxy-4-(4-methyl-imidazol-1-yl)-phenyl]-amine;

[4,6-bis-(2-trifluoromethyl-phenoxy)-[1,3,5]triazin-2-yl]-[3-methoxy-4-(4-methyl-imidazol-1-yl)-phenyl]-amine; and

[4-(4-chloro-benzyloxy)-6-methoxy-[1,3,5]triazin-2-yl]-[3-methoxy-4-(4-methyl-imidazol-1-yl)-phenyl]-amine or a pharmaceutically active acid addition salt thereof.

3. A compound selected from the group consisting of

N-(4-chloro-phenyl)-6-methoxy-N'-[3-methoxy-4-(4-methyl-imidazol-1-yl)-phenyl]-[1,3,5]triazine-2,4-diamine;

N-(4-chloro-phenyl)-6-methoxy-N'-[3-methoxy-4-(4-methyl-imidazol-1-yl)-phenyl]-N-methyl-[1,3,5]triazine-2,4-diamine;

N-(4-chloro-phenyl)-N'-[3-methoxy-4-(4-methyl-imidazol-1-yl)-phenyl]-N-methyl-[1,3,5]triazine-2,4-diamine; and N-(4-chloro-phenyl)-6-isopropoxy-N'-[3-methoxy-4-(4-methyl-imidazol-1-yl)-phenyl]-N-methyl-[1,3,5]triazine-2,4-diamine or a pharmaceutically active acid addition salt thereof.

4. A pharmaceutical composition comprising a therapeutically effective amount of a compound selected from the group consisting of

[3-methoxy-4-(4-methyl-imidazol-1-yl)-phenyl]-(4-methoxy-6-piperidin-1-yl-[1,3,5]triazin-2-yl)-amine;

(1-{4-methoxy-6-[3-methoxy-4-(4-methyl-imidazol-1-yl)-phenylamino]-[1,3,5]triazin-2-yl}-piperidin-4-yl)-acetic acid ethyl ester;

(1-{4-methoxy-6-[3-methoxy-4-(4-methyl-imidazol-1-yl)-phenylamino]-[1,3,5]triazin-2-yl}-piperidin-4-yl)-acetic acid;

[3-methoxy-4-(4-methyl-imidazol-1-yl)-phenyl]-[4-methoxy-6-(2-trifluoromethyl-phenoxy)-[1,3,5]triazin-2-yl]-amine;

[4-(4-fluoro-phenoxy)-6-methoxy-[1,3,5]triazin-2-yl]-[3-methoxy-4-(4-methyl-imidazol-1-yl)-phenyl]-amine;

[3-methoxy-4-(4-methyl-imidazol-1-yl)-phenyl]-[4-methoxy-6-(3,4,5-trifluoro-phenoxy)-[1,3,5]triazin-2-yl]-amine;

[4-(2,4-dichloro-phenoxy)-6-methoxy-[1,3,5]triazin-2-yl]-[3-methoxy-4-(4-methyl-imidazol-1-yl)-phenyl]-amine;

[4-(2-chloro-pyridin-3-yloxy)-6-methoxy-[1,3,5]triazin-2-yl]-[3-methoxy-4-(4-methyl-imidazol-1-yl)-phenyl]-amine;

[4-isopropoxy-6-(2-trifluoromethyl-phenoxy)-[1,3,5]triazin-2-yl]-[3-methoxy-4-(4-methyl-imidazol-1-yl)-phenyl]-amine;

(4,6-diisopropoxy-[1,3,5]triazin-2-yl)-[3-methoxy-4-(4-methyl-imidazol-1-yl)-phenyl]-amine;

[4,6-bis-(2-trifluoromethyl-phenoxy)-[1,3,5]triazin-2-yl]-[3-methoxy-4-(4-methyl-imidazol-1-yl)-phenyl]-amine;

[4-(4-chloro-benzyloxy)-6-methoxy-[1,3,5]triazin-2-yl]-[3-methoxy-4-(4-methyl-imidazol-1-yl)-phenyl]-amine;

N-(4-chloro-phenyl)-6-methoxy-N'-[3-methoxy-4-(4-methyl-imidazol-1-yl)-phenyl]-[1,3,5]triazine-2,4-diamine;

N-(4-chloro-phenyl)-6-methoxy-N'-[3-methoxy-4-(4-methyl-imidazol-1-yl)-phenyl]-N-methyl-[1,3,5]triazine-2,4-diamine;

N-(4-chloro-phenyl)-N'-[3-methoxy-4-(4-methyl-imidazol-1-yl)-phenyl]-N-methyl-[1,3,5]triazine-2,4-diamine; and N-(4-chloro-phenyl)-6-isopropoxy-N'[3-methoxy-4-(4-methyl-imidazol-1-yl)-phenyl]-N-methyl-[1,3,5]triazine-2,4-diamine or a pharmaceutically active acid addition salt thereof and a pharmaceutically acceptable carrier.

* * * * *